United States Patent [19]

Brown et al.

[11] Patent Number: 4,966,837
[45] Date of Patent: * Oct. 30, 1990

[54] METHODS AND COMPOSITIONS FOR THE DETECTION OF FAMILIAL HYPERCHOLESTEROLEMIA

[75] Inventors: Michael S. Brown; Joseph L. Goldstein; David W. Russell, all of Dallas, Tex.

[73] Assignee: Board of Regents, The University of Texas System, Austin, Tex.

[ * ] Notice: The portion of the term of this patent subsequent to May 17, 2005 has been disclaimed.

[21] Appl. No.: 925,702

[22] Filed: Oct. 30, 1986

Related U.S. Application Data

[63] Continuation-in-part of Ser. No. 687,087, Dec. 28, 1984.

[51] Int. Cl.$^5$ .................. C12Q 1/68; C12P 19/34; C12N 15/00; G01N 33/566
[52] U.S. Cl. ..................................... 435/6; 435/91; 435/803; 436/501; 436/811; 530/808; 530/825; 935/9; 935/19; 935/77; 935/78; 935/86; 536/27
[58] Field of Search ................... 435/6, 803, 91; 436/501, 811; 935/78, 9, 19, 77; 530/808, 825

[56] References Cited

U.S. PATENT DOCUMENTS 4,358,535 11/1982 Falkow et al. .
4,395,486 7/1983 Wilson et al. .
4,745,060 5/1988 Brown et al. .................. 935/72 X

FOREIGN PATENT DOCUMENTS

0126544A2 11/1984 European Pat. Off. .

OTHER PUBLICATIONS

Horsthemke, B. et al., Hum. Genet. 71:75–78 (1985).
Chem. Abst. 106, No. 3, Issued Jan. 19, 1987, p. 494, 100449d Humphries, S. E. et al., "DNA Deletions... Diagnosis".
Humphries, S. E. et al., Verh. Dtsch. Ges. Inn. Med. 92:397–401 (1986).
Wieringa et al., (1981) Nucl. Acids Res., 9:489–501.
Goldstein et al., (1982) Medical Clinics of North America, 66:335–362.
Schneider et al., (1982) Jrnl. Biol. Chem. 257:2664–2673.
Tolleshaug et al. (1982) Cell, 30:715:724.
Schneider et al. (1983) Mol. Biol. Med., 1:353–367.
Tolleshaug et al. (1983) Cell, 32:941–951.
Russel et al., (1983) Proc. Natl. Acad. Sci, U.S.A., 80:7501–7505.
Russell et al., (1984) Cell, 37:577–585.
Yamamoto et al., (1984) Cell, 39:27–28.
Lehrman et al. (1985) Science, 227:140–146.
Sudhof et al. (1985), Science, 228:815–822.
Sauls et al. (1985), Clin. Chem., 31:804–811.
Lehrman et al., (1985), Cell, 41:735–743.
International Search Report for International Application No. PCT/US 85/02461, Apr. 24, 1986.
Yamamoto et al. (1986), Science, 232:1230–1237.
Lehrman et al. (1986), Proc. Natl. Acad. Sci. U.S.A., 83:3679–3683.
Kingsley et al. (1986), Jrnl. Cell Biol., 102:1576–1585.
Kingsley et al. (1986), Cell, 44:749–759.

Primary Examiner—Amelia Burgess Yarbrough
Assistant Examiner—Ardin Marschel
Attorney, Agent, or Firm—Arnold, White & Durkee

[57] ABSTRACT

Recombinant DNA transfer vectors containing DNA inserts which are complementary to either the human LDL receptor gene, or its mRNA transcript, are disclosed. Also disclosed are methods which utilize these genetic probes for diagnosing Familial Hypercholesterolemia (FH) in a suspected individual. A case study of numerous such individual are disclosed wherein the genetic deletion mutation is detailed with great precision through the practice of this invention.

26 Claims, 16 Drawing Sheets

```
        -13  AGAGGCTGCGAGCATGGGGCCCTGGGCCTGGAAATTGCGCTGGACCGTCGCCCTTGCTCCTCGCCGCGGGGACT    63
                             MetGlyProTrpGlyTrpLysLeuArgTrpValAlaLeuLeuAlaLeuAlaGlyThr
                             -20                       -10                        -1

CAGGATGGCTCTGATGAGTCCAGGAGAGTGGGAAGACGTGCTGTGTCTGTCACCTTCAAATCCGGGACTTCAGCTGTLysLysSerValThr(Lys)LysSerGlyAspPheSer       243
GlnAspGlySerGlnGluTyrAspGlySerGlnGluTyrAspGlyLeuSerGlyThr(Lys)LysSerValThr(Lys)LysSerGlyAspPheSer(Lys)LysSerGlyAspPheSer
                    40                              50                          60

GAGTTTCGCTGCCACGATGGGAAGTGCATCTCTCGGCAGTTCGTCGTCAGCTCGTGACTCAGATCGTGACTCTGGAGGCCTCAGACGAGGCC    423
GluPheArg(Lys)HisAspGlyLysLys(Lys)IleSerArgGlnPheVal(Lys)SerArgAspArgAsp(Lys)LeuAspGlySerAspGluAla
             100                            110                          120

TGCGAAGATGGCTCGAGCCGCCGGGCCCCGGAGGCCCCGGAGGCCCGGAGTAGGGTCTTTACGTGTTCCAAGGGACATAGGGTCTTTACGTGTTCCAAGGGACATAGCCCCTGCCTCGGCCTTCGAG    603
GluAspGlySerAspGlyLeuSerArgAspAsnSerArgAsnArgAspLysArg(Lys)ArgGlyArgGluTyrValPheGlnGlyAspSerSerPro(Lys)SerAlaPheGlu
                     160                            170                         180

GTGGCCACCTGTCGCCCTGACGAATTCCAGTGCTCTGAGGAAACTGCATCCATGGCAGCGGCCAGTGACAGTGAAATGACTCGC(Lys)    783
ValAlaThr(Lys)ArgProAspGluPheGln(Lys)SerAspGlyPhe(Lys)(Lys)IleHisGlySerArgGln(Lys)AspArgArgGluTyrAsp(Lys)
                220                            230                          240

GACAAAGTCTGCAACATGGCTAGAGACTGCAGATGGTCAGATGAACCCATCAAAGAGTCGGGGACCAACGAATGCTTGGACAAC    963
AspLysVal(Lys)AsnMetAlaArgAsp(Lys)Arg(Lys)AspTrpSerAspGluProIleLysGlyThrAsnGlu(Lys)LeuAspAsn
             280                               290                          300

GAAGATATCGATGAGTGTCAGGATGTCAGGATCCCGACACCTGAACCTGGAACCTGAACCCTGGAGGGTGGCTACAAGTGCCAGTGTGAGGAA    1143
GluAspIleAspGlu(Lys)(Lys)ValGlnAspProAspThr(Lys)SerGlnLeu(Lys)ValAsnLeuGlyLeuValAsnLeuGlyLeuLeu(Lys)TyrLys(Lys)GlnValLysGluGlu
                340                             350                         360

ACGCTGGACCGGAGCGAGTACACCAGCTCTCATCCCAACCTGAGGAACGTGGTCGCTCTGGACACGGAGGTGGCCAGCAATAGAATC    1323
ThrLeuAspArgSerGluTyrThrSerLeuIleProAsnLeuArgAsnValValAlaLeuAspThrGluValAlaSerAsnArgIle
                400                             410                         420

ATCCAGGGCCCCCAGCGGGGATCGTGGATGGATGTGTGAACTGAATCAAGAAGGGTACTGGATGGATGTGTGAACTGAATCAAGAAG    1503
IleGlnAlaProGlyLeuAlaValAspIleProIleHisSerAsnIleTyrTrpThrAspSerValLeuGlyThrValSerValAla
                460                              470                          480

TGGACTGACTGGGGAACTCCGCCAAGATCAAGAAGAGGGCCTGAATGGTGTGGACATACTCGTGGTGACTGAAAACATTCAG    1683
TrpThrAspTrpGlyThrProGlyThrProGlyIleLysLysLysGlyLeuAsnGlyValAspIleLeuValValThrGluGln
                520                              530                         540

GGCAACCGGAAGACCATCTTGGAGGATGAAAGAGGCTGGCCCCACCCCTTCCTTGGCCGTCTTTGAGGACAAAGTATTTGGACA    1863
GlyAsnArgLysThrIleLeuGluAspGluArgGlyTrpProProThrProPheLeuAlaValPheGluAspLysValPheTrpThr
                580                             590                         600

GTCCTCTTCCACAACCTTCACCCAGGCCAAGAGGAGGAGGACTGAACTGGTGTGAGGAGGACCACCTTCTGAGAGGAGGACTCGTGC    2043
ValLeuPheHisAsnLeuThrGlnProArgGlyValAsnTrp(Lys)GluArgThrThrLeuSerAsnGlyGlyTyrGlnTyrLeu(Lys)
                640                             650                          660
```

FIG. 3C

```
CTCCCTGCCCCGCAGATCAACCCCCACTCGCCCAGTTACTGCCGCCTGCCCGGACGGCATGCTGTGGCCAGGGACATGAGGAGCTGCCTC
LeuProAlaProGlnIleAsnProHisSerProLysPheThr(Lys)AlaArgAspGlyMetLeuLeuAlaArgAspMetArgSer(Lys)Leu
661                              670                              680                              690

ACCACCCGGCCTGTTCCCGACACCTCCCGGCTGCCTGGGCCACCTGGGCTCACCACGGTGGAGATAGTGACAATGTCTCACCAAGCTCTG
ThrThrArgProValProAspThrSerArgLeuProGlyAlaThrTrpGlyLeuThrThrValGluIleValThrMetSerHisGlnAlaLeu
721                              730                              740                              750

CTTTGCTGGGGTCTTCCTTCTATGGAGAACTGGGGGCTTAAGAGAACATCAACAGCATCAACTTTGACAACCCGTCTATCAGAAGACCACA
LeuCys(Lys)ValIlePheLeuLeuTrpLysAsnTrpArgLeuLysAsnIleAsnPheAspAsnProValTyrGlnLysThrThr
781                              790                              800                              810

ACATCTGCCTGGAGTCCCGCCCCTGCTGGAGTCCCAGAACCCTTCCTGAGACCTTGTTTTATTCAAAGACAGAGAAGACAAAGCATTGCC

TGGTTCTTCCTTCCTGTGAAGGATAAAGACAGGCCCTGGGGACCAGGATGACACCTCCATTCTCTCCAGGAAGTTTGAGTTTCTD

GCAGATGGCACCAACGGGACCCCCTGGCCTCATCCACCAATCTCTAAGCCAAACCCCTAAACTCAGGAGTCAACGTGTTTACCTCTTC

TACCTTCCTTAAGCCAGGAAAGGGATTCATGGCGTGTCAGGACACCAGCCTGGTGCCCATCTCCCGACCCCTACCACTTCCATTCCCGTGGTCTCCTT

GACACGTGGCCTGCACCCAGGTGTGGCCAGGGCCTGTCAATGAATGCCGGGGACAGAGAGGGGCAGGTTGACGGGACTTCAAAGCCGTGATCGTGAATATC

GGGATCCCAGGCCAGGGAAAGCCCGTGTCAATGAATGCCGGGGACAGAGAGGGGCAGGTTGACGGGACTTCAAAGCCGTGATCGTGAATATC

TGTCGTTGATGGGTATGTGTTTAAAAACATGCACGGTCACGGCCCGGGCGCAGTGCCTCACGCCCTGTAATCCCAGCACTTTGGGAGGCCGAGGCG

CGCGGGGTGGGCACCTGTAGTCCCAGCTACTCGGGAGGCTGAGGCAGGAGAATGGTGTGAACCCGGGAAGCGGAGCTTGCAGTGAGCCGAGA

TGCATCAGCAGCCCATGGCCTCTGG CAGGCATGGCGAGGCTGAGCTGGATCACTTGAGTTCAGGAGTTGGAGACCAGGCCTGAGCAACAAAGCGAGATCCCATCTCTAC

TGTAATCCCAGCACTTTGGGAGGCTGAGGCATTGAGGCTGTCGTGAGCTATG

TGAGCCCAGGAGGTGGAGGTTGCAGTGAGCCATGATCGAGCCATGATCGAGCCACTGCACTCCAGCCTGGGCAACACATGAAGACCCTATTC AGAAATACAAC

ATGTCCGGAGAGACAGTGACAGGCCTCCGTCAGACTCCCGCGTGAAGATGTCACAAGGGATTGGCAATTGTCCCCAGGACAAAACACTGTGTC

TGTTTGCACTTTGTATATTGGTTGAAACTGTTATCACTTATATATATATATATATATATATATATAATCTATTTATTTTGCAAACCCTGG

TTTGCACGAACTGGACTGTGTGCAACGCTTTTGGGAGAATGATGTCCCCGTGTATGTATGAGTGGCTTCTGGGAGAGAGTGGGTGTCACTTTT
```

FIG.3D

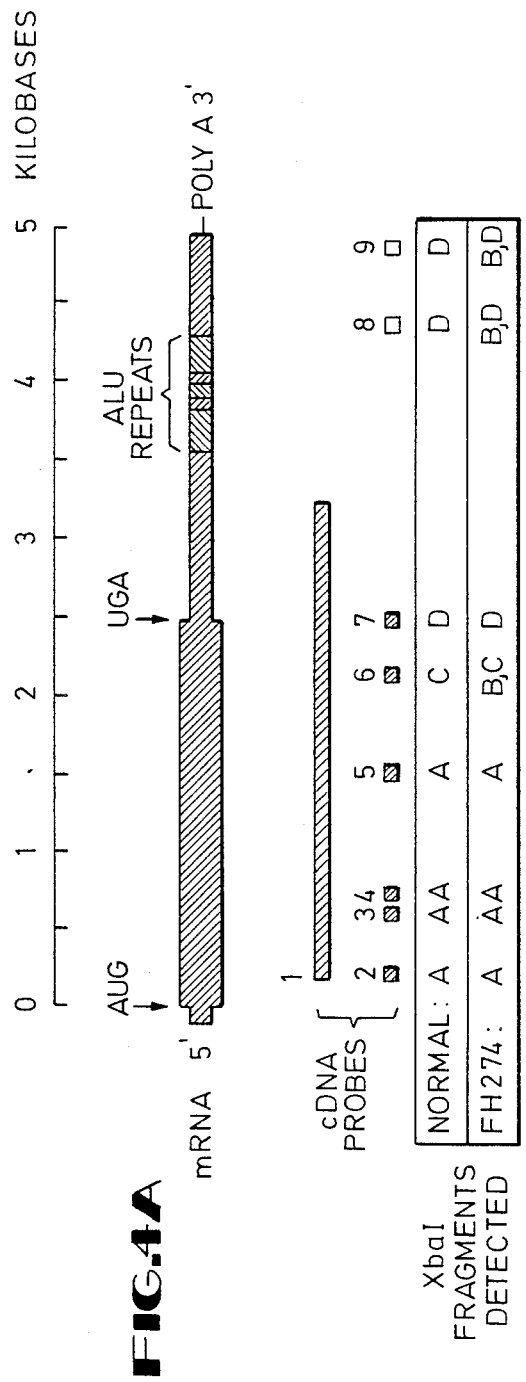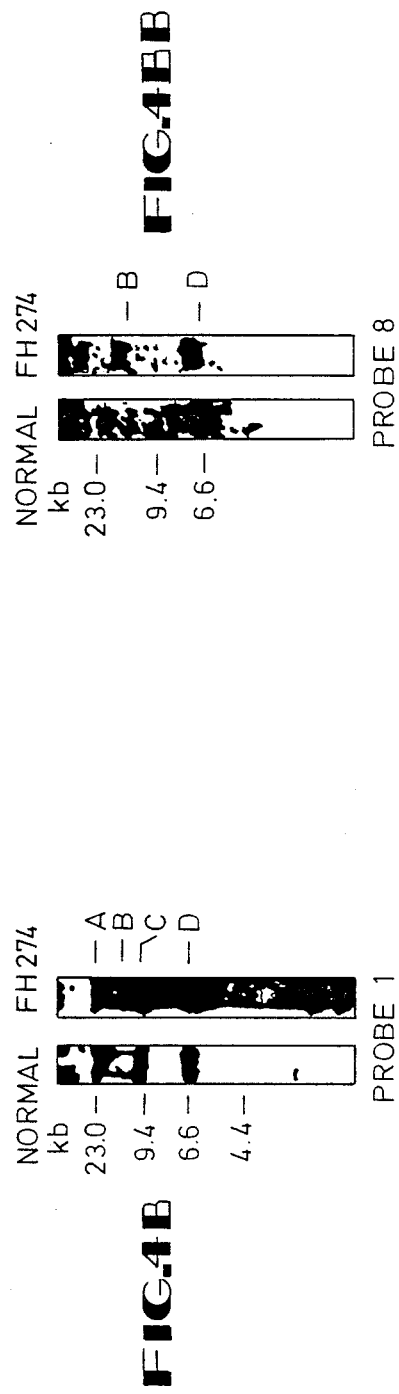

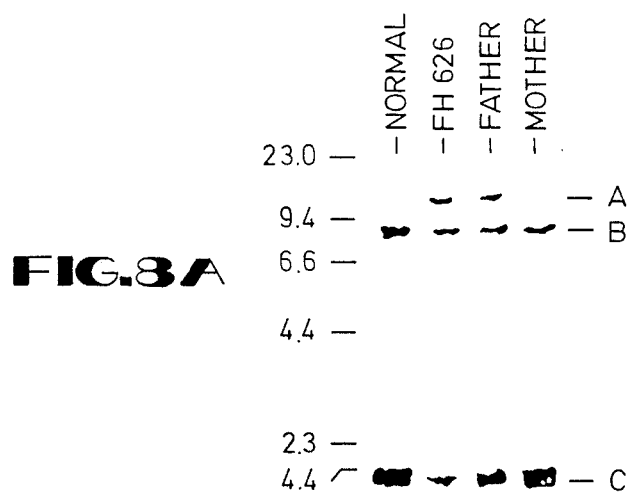
FIG. 8A
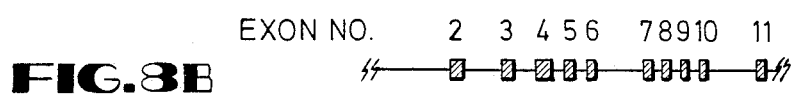
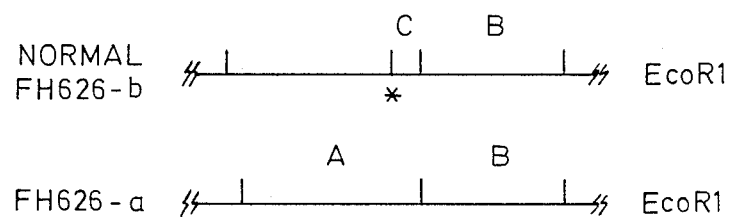
FIG. 8B
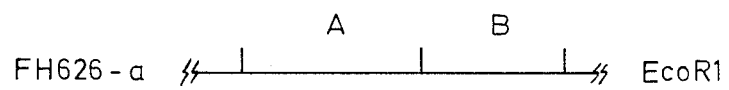
FIG. 9
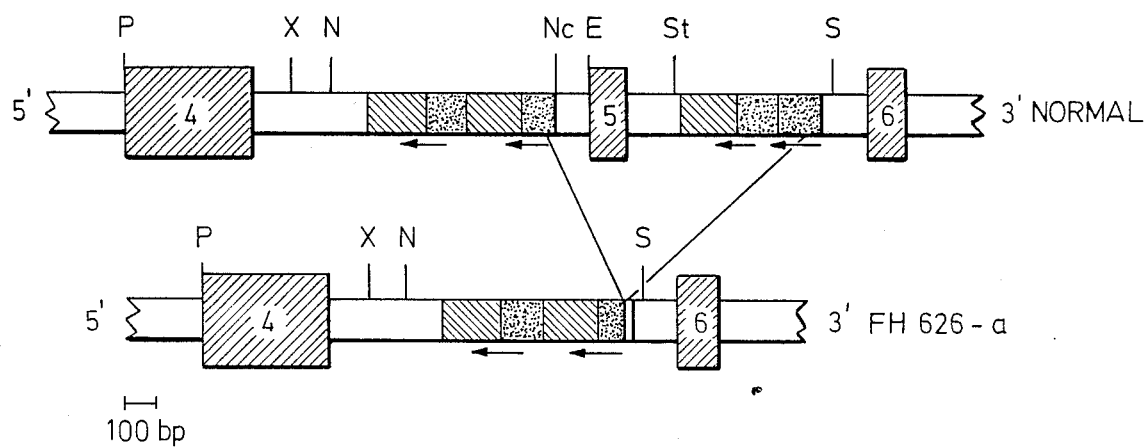

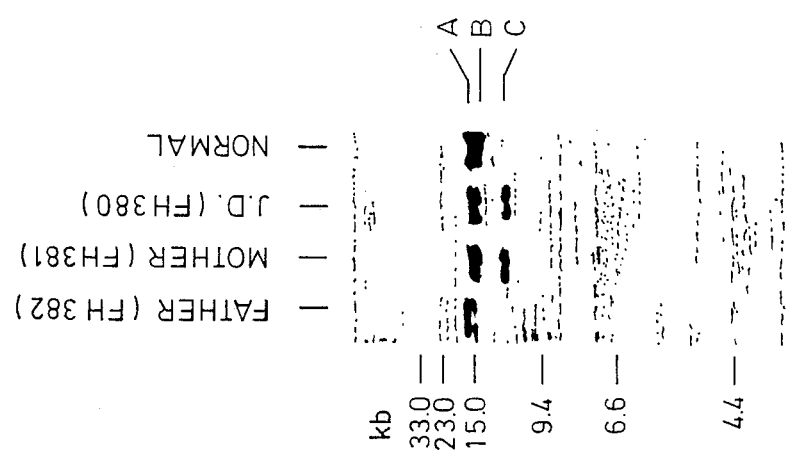
FIG. 12
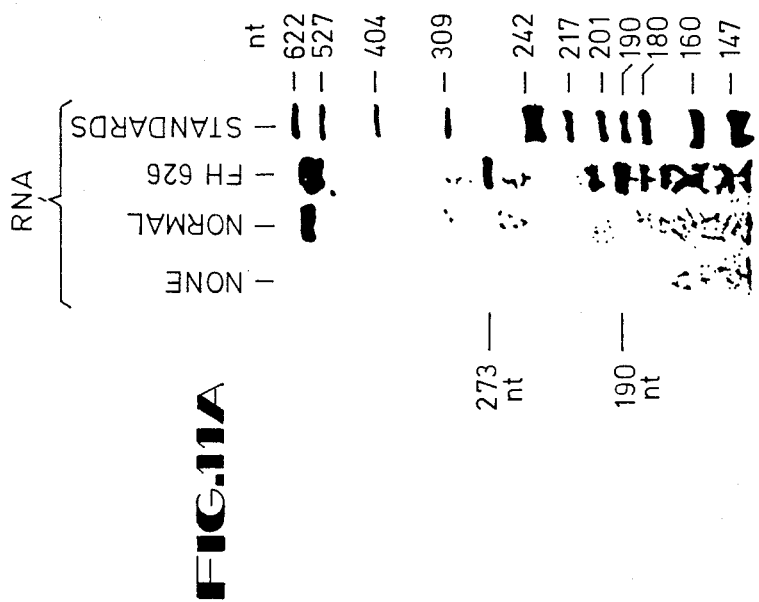
FIG. 11A
FIG. 11B

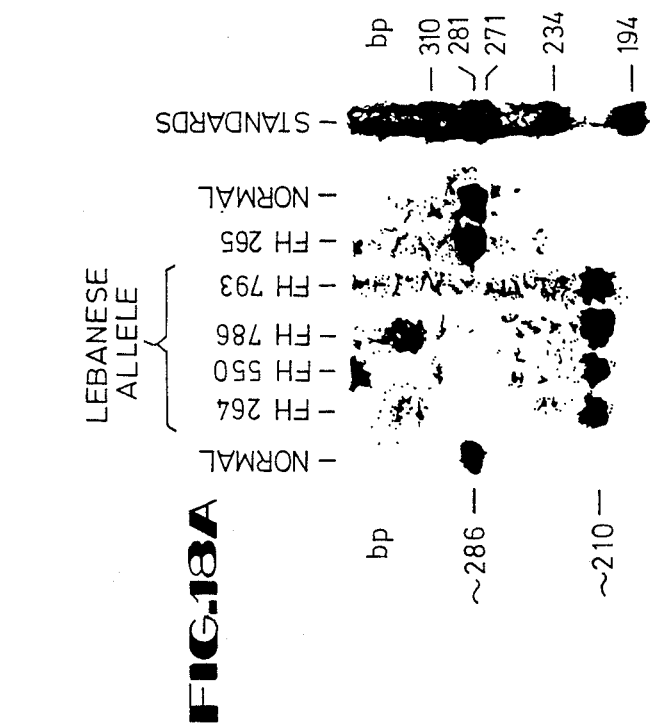
FIG. 18A
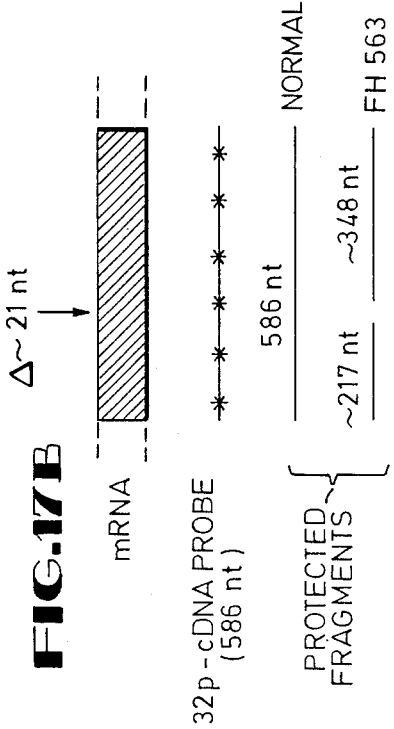
FIG. 18B
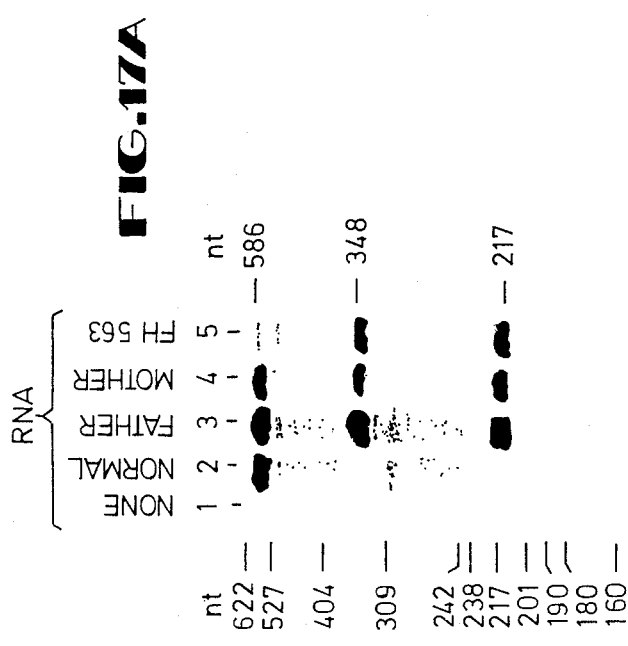
FIG. 17A
FIG. 17B

METHODS AND COMPOSITIONS FOR THE DETECTION OF FAMILIAL HYPERCHOLESTEROLEMIA

The government may own certain rights in the present invention pursuant to National Institutes of Health grant numbers HL20948 and HL31346.

BACKGROUND OF THE INVENTION

The present application is a continuation-in-part of U.S. Ser. No. 687,087, filed Dec. 28, 1984.

The present invention is directed towards methods and compositions useful in the diagnosis of a genetic predisposition towards the development of hypercholesterolemia, atherosclerosis, and eventually, heart disease. More particularly, the present invention is directed towards recombinant DNA molecules which serve as useful probes in detecting the presence of mutant low density lipoprotein (LDL) receptor genes in individuals suspected of having familial hypercholesterolemia (FH).

Half of all deaths in the U.S. are caused by atherosclerosis, the disease in which cholesterol, accumulating in the wall of arteries, forms bulky plaques that inhibit the flow of blood until a clot eventually forms, obstructing an artery and causing a heart attack or a stroke. The cholesterol of atherosclerotic plaques is derived from particles called low-density lipoprotein (LDL) that circulate in the bloodstream. The more LDL there is in the blood, the more rapidly atherosclerosis develops.

Epidemiologic data reveal the surprising fact that more than half of the people in Western industrialized societies, including the U.S., have a level of circulating LDL that puts them at high risk for developing atherosclerosis. Because such concentrations are so prevalent, they are considered "normal," but clearly they are not truly normal. They predispose to accelerated atherosclerosis and heart attacks or strokes.

Some answers as to why the LDL levels are so dangerously high in many Americans are emerging from studies of specialized proteins, called LDL receptors. These receptors project from the surface of animal cells. The receptors bind LDL particles and extract them from the fluid that bathes the cells. The LDL is taken into the cells and broken down, yielding its cholesterol to serve each cell's needs. In supplying cells with cholesterol the receptors perform a second physiological function, which is critical to the prevention of atherosclerosis: they remove LDL from the bloodstream.

The number of receptors displayed on the surface of cells varies with the cells' demand for cholesterol. When the need is low, excess cholesterol accumulates; cells make fewer receptors and take up LDL at a reduced rate. This protects cells against excess cholesterol, but at a high price: the reduction in the number of receptors decreases the rate at which LDL is removed from the circulation, the blood level of LDL rises and atherosclerosis is accelerated.

It has been proposed that the high level of LDL in many Americans is attributable to a combination of factors that diminish the production of LDL receptors. Recognition of the central role of the receptors has led to a treatment for a severe genetic form of atherosclerosis, and it has also shed some light on the continuing controversy over the role of diet in atherosclerosis in the general population.

LDL is a large spherical particle whose oily core is composed of some 1,500 molecules of the fatty alcohol cholesterol, each attached by an ester linkage to a long-chain fatty acid. This core of cholesterol esters is enclosed in a layer of phospholipid and unesterified cholesterol molecules. The phospholipids are arrayed so that their hydrophilic heads are on the outside, allowing the LDL to be dissolved in the blood or intercellular fluid. Embedded in this hydrophilic coat is one large protein molecule designated apoprotein B-100.

It is apoprotein B-100 that is recognized and bound by the LDL receptor, a glycoprotein (a protein to which sugar chains are attached). The receptor spans the thickness of the cell's plasma membrane and carries a binding site that protrudes from the cell surface. Binding takes place when LDL is present at a concentration of less than $10^{-9}$ molar, which is to say that the receptor can pick out a single LDL particle from more than a billion molecules of water. The receptor binds only lipoproteins carrying apoprotein B-100 or a related protein designated apoprotein E.

In 1976 it was discovered that the LDL receptors are clustered in specialized regions where the cell membrane is indented to form craters known as coated pits (because the inner surface of the membrane under them is coated with the protein clathrin). Within minutes of their formation the pits pouch inward into the cell and pinch off from the surface to form membrane-bounded sacs called coated vesicles; and LDL bound to a receptor is carried into the cell. Receptor-mediated endocytosis, the term applied to this process of uptake through coated pits and vesicles, is now being recognized as a general mechanism whereby cells take up many large molecules, each having its own highly specific receptor.

Eventually the LDL is separated from the receptor (which is recycled to the cell surface) and is delivered to a lysosome, a sac filled with digestive enzymes. Some of the enzymes break down the LDL's coat, exposing the cholesterol ester core. Another enzyme clips off the fatty acid tails of the cholesterol esters, liberating unesterified cholesterol, which leaves the lysosome. All cells incorporate the cholesterol into newly synthesized surface membranes. In certain specialized cells the cholesterol extracted from LDL has other roles. In the adrenal gland and in the ovary it is converted into respectively the steroid hormones cortisol and estradiol; in the liver it is transformed to make bile acids, which have a digestive function in the intestine.

The central role of the LDL receptor in atherosclerosis was first appreciated in 1974 when it was shown that absence of the receptor was responsible for the severe disease called familial hypercholesterolemia (FH). Much earlier, in 1939, Carl Muller of the Oslo Community Hospital in Norway identified the disease as an inborn error of metabolism causing high blood cholesterol levels and heart attacks in young people; he recognized that it is transmitted as a dominant trait determined by a single gene. In the 1960's two forms of the disease were delineated, a heterozygous form and a more severe homozygous form. Heterozygotes, who inherit one mutant gene, are quite common: about one in 500 people in most ethnic groups. Their plasma LDL level is twice the normal level (even before birth) and they begin to have heart attacks by the time they are 35; among people under 60 who have heart attacks, one in 20 has heterozygous FH.

If two FH heterozygotes marry (one in 250,000 marriages), each child has one chance in four of inheriting two copies of the mutant gene, one from each parent. Such FH homozygotes (about one in a million people) have a circulating LDL level more than six times higher than normal; heart attacks can occur at the age of two and are almost inevitable by the age of 20. It is notable that these children have none of the risk factors for atherosclerosis other than an elevated LDL level. They have normal blood pressure, do not smoke and do not have a high blood glucose level. Homozygous FH is a vivid experiment of nature. It demonstrates unequivocally the causal relation between an elevated circulating LDL level and atherosclerosis.

Heterozygotes with familial hypercholesterolemia can often be suspected at birth because blood plasma from the umbilical cord contains a two- to three-fold increase in the concentration of LDL-cholesterol. The elevated levels of plasma LDL persist throughout life, but symptoms typically do not develop until the third or fourth decade. The most important clinical feature is premature and accelerated coronary atherosclerosis. Myocardial infarctions begin to occur in affected men in the third decade, showing a peak incidence in the fourth and fifth decades. By age 60, approximately 85% have experienced a myocardial infarction. In women the incidence of myocardial infarction is also elevated, but the mean age of onset is delayed 10 years in comparison to men. Heterozygotes for familial hypercholesterolemia constitute about 5% of all patients who have a myocardial infarction.

Xanthomas of the tendons are the second major clinical manifestation of the heterozygous state. These xanthomas are nodular swellings that typically involve the Achilles and other tendons about the knee, elbow, and dorsum of the hand. They are formed by the deposition of LDL-derived cholesterol esters in tissue macrophages are swollen with lipid droplets and form foal cells. Cholesterol is also deposited in the soft tissue of the eyelid, producing xanthelasma, and within the cornea, producing arcus lipoides corneae. Whereas tendon xanthomas are essentially diagnostic of familial hypercholesterolemia, xanthelasma and acrus lipoides corneae are not specific. The latter abnormalities also occur in many adults with normal plasma lipid levels. The incidence of tendon xanthomas in familial hypercholesterolemia increases with age. Eventually, about 75% of affected heterozygotes display this sign.

Homozygote individuals have marked elevations in the plasma level of LDL from birth. A unique type of planar cutaneous xanthoma is often present at birth and always develops within the last six years of life. These cutaneous xanthomas are raised, yellow plaque-like lesions that occur at points of cutaneous trauma, such as over the knees, elbows, and buttocks. Xanthomas are almost always present in the interdigital webs of the hands, particularly between the thumb and index finger. Tendon xanthomas, arcus lipoides corneae, and xanthelasma are also characteristic. Coronary artery atherosclerosis frequently has its clinical onset in homozygotes before age 10, and myocardial infarction has been reported as early as 18 months of age. In addition to coronary atherosclerosis, cholesterol is frequently deposited in the aortic valve, producing symptomatic aortic stenosis. Homozygotes usually succumb to the complications of myocardial infarction before age 30.

One in 500 persons in most populations has a mutation in the LDL receptor gene that destroys the function of the gene and produces the clinical syndrome of heterozygous familial hypercholesterolemia. Many of these mutant genes fail to produce any detectable receptors. Other mutant genes produce a small number of receptors; still other mutant genes produce essentially normal numbers of defective receptors that do not bind LDL properly. In other affected individuals, an LDL receptor protein of abnormal length is produced. Whereas the normal precursor form of the receptor displays an apparent molecular weight of approximately 120,000 daltons when measured by gel electrophoresis, aberrant forms of the protein encoded by mutant genes have been identified that migrate at apparent molecular weights of 100,000, 135,000 and 170,000 daltons. It is possible that such mutations observed in the LDL receptor protein may be the result of deletion or insertion mutations in the gene responsible for LDL receptor production. All of the above described mutations are felt to reside in or near the gene for the LDL receptor. Thus, a means of identifying directly those individuals who carry a mutant LDL receptor gene would greatly facilitate our ability to identify those individuals with a genetic predisposition towards developing atherosclerosis and heart disease. These mutations could be identified if a complementary DNA (cDNA) for the receptor gene were discovered.

BRIEF DESCRIPTION OF THE FIGURES

FIG. 3 displays the nucleotide sequence of the cDNA corresponding to the human LDL receptor mRNA and the predicted amino acid sequence of the receptor protein. The nucleotides are numbered on the right-hand side in the 5'-to-3' direction; nucleotide 1 is the A of the ATG codon that encodes the initiator methionine; negative numbers refer to the 5' untranslated region. The amino acids are numbered underneath the sequence; residue 1 is the alanine found at the $NH_2$ terminus of the mature protein; negative numbers refer to the cleaved signal sequence. The signal sequence (21 residues) and the membrane-spanning sequence (22 residues) are indicated by single solid underlines. The sites to which N-linked carbohydrate could be attached (Asn-X-Ser or Asn-X-Thr) are indicated by double solid underlines. Cysteine residues are circled. A stretch of 48 residues rich in serines and threonines to which O-linked carbohydrate could be attached is indicated by the dotted underlines. The Alu sequences in the 3' untranslated region of the cDNA are boxed; the direct repeats associated with the first Alu sequence are indicated by dotted arrows above the sequence. Three potential polyadenylation signals in the 3' untranslated region are indicated by overlines and underlines.

FIG. 4 is an analysis of Xba I restriction digests of genomic DNA from a normal subject and an individual with familial hypercholesterolemia (designated FH274) with DNA probes from different regions of the LDL receptor cDNA. FIG. 4A is a diagram of the mRNA for the human LDL receptor which is shown with AUG and UGA indicating the beginning and end of the translated region, respectively. The sizes and locations of the $^{32}$P-labeled cDNA probes used to map the LDL receptor gene are shown by the closed bars and are numbered 1–9. FIG. 4B is an autoradiograph of a Southern blot of either normal or mutant (FH 274) genomic DNA following hybridization with either probe 1 (left) or probe 8 (right). The Xba I restriction fragments are designated A-D along the right side of each blot. Molecular size standards were generated by Hind III cleavage of bacteriophage DNA and are indicated to the left of each blot. The Xba I fragments detected by probes 2-9 in the normal subject and FH 274 are indicated at the bottom of FIG. 4A.

FIG. 8 is a Southern blot hybridization of genomic DNA isolated from patent FH 626 and his parents. The positions to which HindIII fragments of bacteriophage lambda DNA migrated and their sizes in kilobases are indicated on the left side of the figure. In the autoradiogram, band A contains exons 2, 3, 4, and 6; band B contains exons 7 through 10; and band C includes exons 5 and 6. An EcoRI restriction map of the LDL receptor gene in the region of exons 2 through 11 is shown below the autoradiogram. The asterisk (*) in the normal gene denotes the position of the EcoRI site that is missing in the deletion-bearing FH 626-a allele and the 5' start site of the $^{32}$P-labeled probe that was used in the experiment.

FIG. 9 is a comparative map of FH 626-a and the normal LDL gene. The figure illustrates the particular deletion mutation exhibited by FH 626-A.

FIG. 11 demonstrates S1 nuclease mapping of RNA isolated from normal and FH 626 cells. Total RNA isolated from normal cells (10 ug) or from FH 626 cells (20 ug) was hybridized to a $^{32}$P-labeled single-stranded cDNA probe corresponding to nucleotides 422-1007 of the normal LDL receptor cDNA, after which the RNA-DNA hybrids were digested with 700 units of S1 nuclease as described. Following electrophoresis of the S1-resistant hybrids, the dried gel was used to expose Kodak XAR-5 film in the presence of an intensifying screen for 24 h at −70° C. Radiolabeled standards were derived from an MspI digest of pBR322. A schematic illustrated the results obtained in the experiment is shown below the autoradiogram.

FIG. 12 is a southern blot hybridization of BamHI-cleaved genomic DNA from patient J.D. (FH 380) and his parents. Genomic DNA (5 ug) isolated from cultured fibroblasts from the indicated subject was digested with BamHI, electrophoresed in a 1% agarose gel, transferred to nitrocellulose, and hybridized with a $^{32}$P-labeled probe corresponding to exons 3 through 18 of the LDL receptor gene. The three relevant BamHI restriction fragments are designated A to C. Molecular size standards were generated by HindIII cleavage or Xho I cleavage of bacteriophage lambda DNA. Filters were exposed to x-ray film with an intensifying screen for 18 h at −70° C.

FIG. 17 illustrates the expression of normal and mutant LDL receptor mRNA's in human fibroblasts from FH 563 and his parents. LDL receptor mRNA's were detected by a solution hybridization-Sl nuclease assay. A uniformly 32P-labeled probe encompasing nucleotides 422 to 1007 of the human receptor mRNA was prepared and annealed to the indicated RNA at 39° C. for 16 hours. After digestion with 700 units of Sl nuclease for 1 hour at 37° C. and eectrophoresis on denaturing polyacrylamide gels, nuclease-resistant hybrids were visualized by autoradiography. Each hybridization reaction contained RNA isolated from the following cell strains induced for LDL receptor expression: (lane 10) no RNA; (lane 2) 10 ug of total RNA from SV40-transformed normal human fibroblasts; (lane 3) 15 ug of total RNA from fibroblasts of the father of FH 563; (lane 4) 15 ug of total RNA from fibroblasts from the mother of FH 563; (lane 5) 10 ug of total RNA from fibroblasts of FH 563. The dried gel was exposed to Kodak XAR 5 film for 25 hours at −70° C. with a Dupont Cronex Lighting Plus screen. Size standards were generated by electrophoresis of a labeled Msp I digest of pBR322 DNA.

FIG. 18 illustrates the southern detection of the Lebanese mutation in four patients with classic homozygous FH. Panel A: Genomic DNA (5 ug) from the indicated subject was digested with HinfI, electrophoresed, and blotted. The blot was probed with a single stranded probe that contained a portion of exon 14 of the human LDL receptor gene (corresponding to nucleotides 2014 to 2107 of the human LDL receptor cDNA). The sizes of the fragments detected were estimated from their migration relative to standards obtained by digestion of )X174 replicative form DNA with HaeIII. The filter was exposed to x-ray film for 10 days. Panel B shows the site of the mutation in exon 14 and the predicted fragment sizes after HinfI digestion.

SUMMARY OF THE INVENTION

Figure 1:
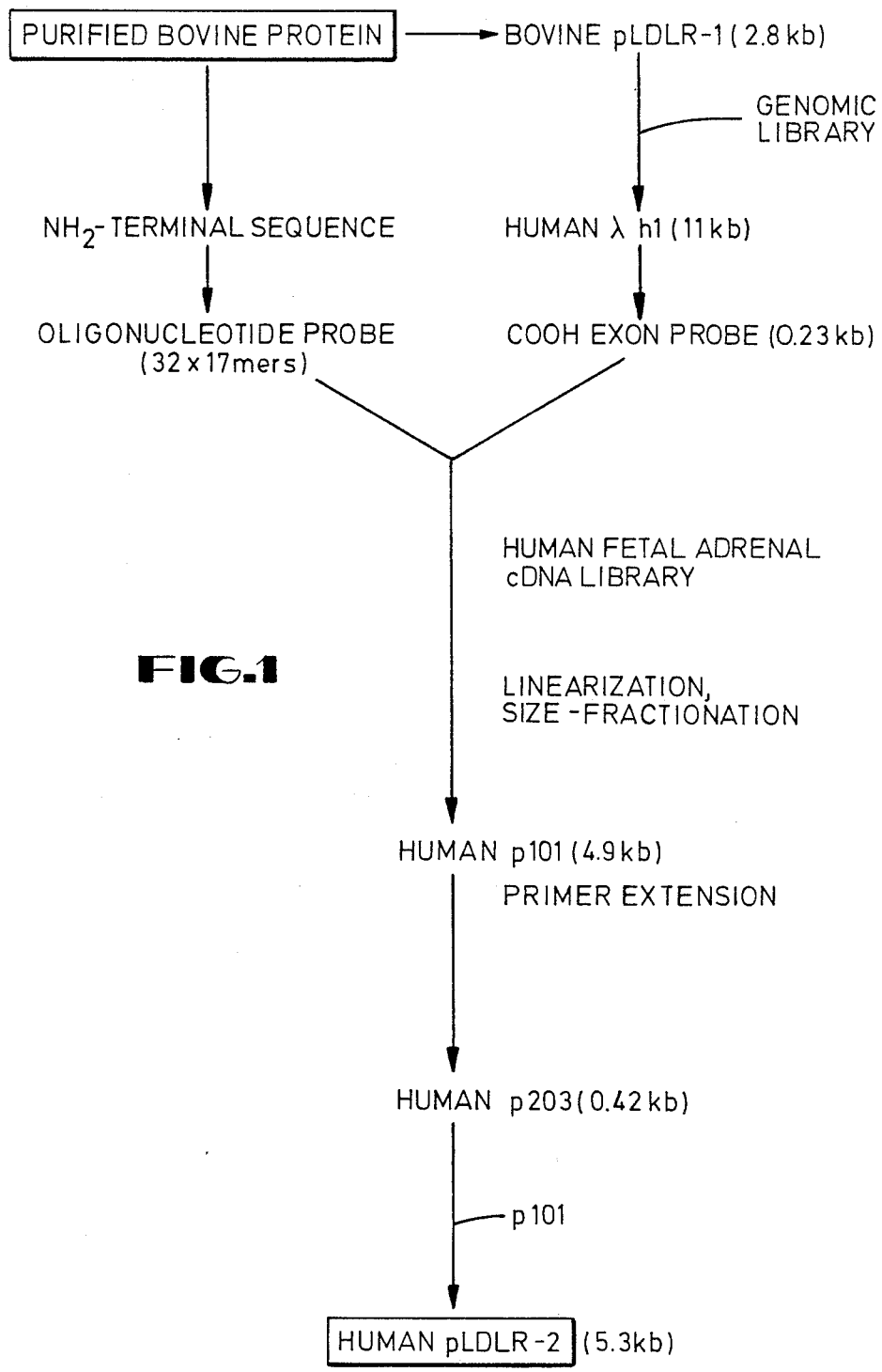
FIG. 1 is a schematic representation of the cDNA cloning strategy used in cloning the human LDL receptor. Human hl is a partial genomic clone corresponding to the 3' end of the LDL receptor gene. Recombinant plasmids p101 and p203 contain partial cDNA's which are complementary to the human LDL receptor mRNA. Plasmid pLDLR-2 is a fusion construct of p101 and p203 and contains a nearly full-length cDNA for the human LDL receptor mRNA. The numbers in parentheses refer to the lengths of the DNA inserts in a given clone.

The present invention discloses a technique suitable for the construction of recombinant DNA transfer vectors which contain a cDNA sequence corresponding to the mRNA sequence of the human Low Density Lipoprotein (LDL) receptor gene. In addition, the present invention discloses recombinant DNA transfer vectors that contain DNA inserts which are complementary to various portions of either the human LDL receptor gene or the mRNA transcript of that gene.

Recombinant DNA transfer vectors disclosed by the present invention need not necessarily contain the entire human LDL receptor gene in order to be useful in the practice of the invention. Similarly, the recombinant transfer vector need not contain a DNA fragment which is complementary to the entire mRNA transcript for that gene. Recombinant transfer vectors may be constructed of smaller subfragments which are complementary to either the human LDL receptor gene or the mRNA for that gene. In fact, the use of different subfragments of the gene as probes may be necessary for detailing specific mutations in certain FH individuals. All that is required is that these fragments be of sufficient length to form a stable duplex or hybrid. Such fragments are said to be "hybridizable" in that they are capable of stable duplex formation. Generally, DNA fragments at least fourteen nucleotides in length are capable of forming stable duplex's (i.e.—a tetradecamer).

Individuals with Familial Hypercholesterolemia (FH) are diagnosed using the present invention by determining the presence of a mutation in the gene which codes for the LDL receptor. DNA isolated from the recombinant cDNA clones has been used to diagnose numerous patients with familial hypercholesterolemia who have mutations in the gene. However, the cDNA, or fragments thereof, should also be useful in diagnosing almost all mutations, including those resulting from single nucleotide changes (point mutations).

In general, the method consists of fragmenting the DNA from cells of an individual who is suspected of having a mutation followed by separating the DNA fragments into a pattern according to some physio-chemical property of the DNA, for example, molecular weight or size of the DNA fragments. The separated DNA is then hybridization probed with labeled LDL receptor DNA in order to identify those fragments of DNA from the individual which correspond to the LDL receptor gene. Then, by comparing the pattern of LDL receptor gene fragments of the suspected individual to a similar fragment pattern from a normal individual, it can be determined whether the suspected individual displays a mutation. If the pattern of LDL receptor gene fragments identified in the suspected individual exhibits an alteration relative to the control pattern, a gene mutation has been detected.

One method which has proved particularly useful in fragmenting the DNA utilizes restriction enzyme digestion. However, other methods, including chemical cleavage of the DNA, could also be used providing that such methods are capable of reproducibly cleaving genomic DNA into the same discrete fragments.

The fragmented DNA can be separated into a recognizable pattern using various methods, the most useful of which take advantage of the varying sizes of the discrete DNA. For example, DNA fragments can be separated according to molecular weight by velocity sedimentation through a density gradient, or, by molecular size by gel exclusion chromatography. However, for the purposes of the present invention, the preferred technique is to separate the DNA fragments by electrophoresis through an agarose or polyacrylamide gel matrix.

The cloned LDL receptor DNA can be conveniently labeled with radioactive nucleides which allow for ready visualization of the corresponding genomic LDL receptor DNA fragment pattern after hybridization and autoradiography. Other labeling techniques, including for example, heavy isotopes, would be possible but would prove cumbersome in practice as a means of identifying the corresponding genomic sequences.

In addition to the use of cloned DNA fragments diagnosis can in principle be made with chemically synthesized oligonucleotides that correspond to portions of the cDNA that are disclosed herein. Genomic DNA from individuals with single base substitutions in the LDL receptor gene will hybridize to such oligonucleotides less strongly than does DNA from a normal individual. Such weakened hybridization will therefore be a method of diagnosis of many patients with FH in both the heterozygous and homozygous forms.

DETAILED DESCRIPTION OF THE PREFERRED EMBODIMENTS

The low density lipoprotein (LDL) receptor is a cell surface protein that plays a central role in the metabolism of cholesterol in humans and animals. Through the process of endocytosis, the LDL receptor is responsible for binding serum cholesterol and making it available for cellular metabolism. This is made possible by internalization of the receptor/cholesterol complex, the cholesterol then being liberated by catabolism of the internalized complex. The liberated cholesterol regulates, via a feedback mechanism, the rate of synthesis of the LDL receptor. The increased demand for cholesterol in certain steroidogenic tissues, such as the adrenal cortex and the ovarian corpus luteum, is met by an increased number of LDL receptors. A foremost distinguishing feature of the LDL receptor is that mutations affecting its structure and function give rise to one of the most prevalent human genetic diseases, familial hypercholesterolemia.

Recombinant DNA technology provides one approach to detecting the presence of mutations in an individual suspected of having FH. By using a probe consisting of a purified human LDL receptor gene, or a hybridizable subfragment thereof, abnormalities present in a particular individual's LDL receptor gene can be identified and that individual can then be targeted for other types of therapy aimed at addressing the symptoms of FH. That is, once FH individuals are identified through processes disclosed by the present invention, these individuals can be targeted for therapy, including both diet modification, pharmacologic approaches, and surgery, all aimed at reducing the levels of circulating cholesterol in these individuals. In addition, knowledge concerning the genetic structure of the LDL receptor gene in FH individuals could eventually lead to more dramatic therapeutic approaches to the disease, including somatic gene replacement or modification.

The first step in understanding and identifying the underlying genetic abnormalities in FH individuals is through the development of suitable probes, using genetic engineering techniques, by which both normal and abnormal LDL receptor genes may be studied. The most ideal genetic probe for studying the structure of the human LDL receptor gene would be a cloned human LDL receptor gene or a cDNA prepared to the receptor mRNA. However, there are difficulties in approaching this problem directly in that it would require isolation of the probe from some human source. This source would preferably be an adrenal or ovarian source where the receptor, and its mRNA, are in greater abundance. This approach is somewhat impractical in that it is difficult to obtain sufficient amounts of the appropriate human tissues. The present invention describes a fortuitous approach whereby the LDL receptor cDNA is cloned from a bovine source and the cloned bovine LDL receptor cDNA is then used to isolate part of the human gene from a gene library. The part of the human gene is then used to isolate nearly full-length human cDNA clones. This was fortuitous in that it was not apparent until after the human cDNA was cloned and sequenced, that the bovine sequences which were used as hybridization probes could be used to correctly probe for the human LDL receptor gene. In retrospect, the homology between the bovine and human gene was sufficient enough to allow for the cloning approach detailed herein.

The isolation of human recombinant DNA clones, bearing copies of the human LDL receptor mRNA, facilitated the development of an assay whereby LDL receptor gene mutations could be detected. To illustrate the utility of this assay, a case study of an individual afflicted with familial hypercholesterolemia (hereinafter designated FH 274) was undertaken. Although the case study described herein goes into extreme detail as to the structure of that individuals specific genetic defect, it is not contemplated by the present invention that such measures will be necessary as a diagnostic approach. However, this material is included herein to illustrate the power of these genetic techniques which are made available by the present invention. Moreover, they provide a means whereby many other defects in the LDL receptor gene may be diagnosed.

Thus, the present invention provides a method whereby not only may the presence of a genetic defect in the LDL receptor gene be identified but, in addition, the particular genetic defect may be detailed with great specification.

The present inventors feel that these techniques provide a method whereby segments of the population as a whole may be screened for the presence of genetic defects in the LDL receptor gene. Once these individuals are identified through the screening procedures detailed herein, the specific abnormalities exhibited by the mutant LDL receptor gene can then be studied in great detail. Therefore, the present Applicants feel that the present invention will lead to a greater future understanding of the genetic events which give rise to the serious and prevalent human genetic disease, Familial Hypercholesterolemia.

EXAMPLE I

Cloning of the Bovine LDL Receptor Gene cDNA

A Bovine LDL receptor gene cDNA clone, hereinafter designated pLDLR-1, was isolated using a combination of polysome immunopurification and oligonucleotide hybridization. Generally, the technique proceeds through five steps. These steps consist of (1) isolation of the bovine receptor protein, (2) generation of a polyclonal antibody capable of reacting with the bovine LDL receptor protein, (3) specific immunoprecipitation of those bovine polysomes which are actively engaged in translation of the bovine receptor mRNA, followed by enriching for the receptor mRNA isolated from the precipitated polysomes, (4) preparation of a cDNA clone bank from the enriched mRNA, (5) screening of the cDNA clone bank to isolate a representative clone bearing a bovine LDL receptor cDNA insert. These steps are described in detail as follows.

Bovine Receptor Isolation and Generation of a Polyclonal Antibody

Homogeneous LDL receptor protein was isolated from bovine adrenal cortex as described by Schneider, et al., *J. Biol. Chem.*, 257:2664–2673 (1982), incorporated herein by reference. A polyclonal antibody against the bovine adrenal LDL receptor was raised in rabbits and purified on staphylococcal protein A-sepharose as described by Tolleshaug, et al. *Cell,* 30:715–724 (1982), incorporated herein by reference. This antibody and its corresponding non-immune rabbit IgG were free of gross RNase contamination as shown by their failure to alter the sedimentation behavior of polysomes or sucrose gradients.

Polysome Immunoprecipitation of Bovine LDL Receptor mRNA

Polysomes enriched in mRNA for the LDL receptor were prepared as follows. Bovine tissue was frozen in liquid nitrogen within 5 min of slaughter. Adrenal glands were powdered in liquid nitrogen in a Waring blender and stored at $-70°$ C. prior to polysome isolation.

Ten-gram aliquots of powdered adrenals were homogenized with a Brinkmann Polytron in 42 ml of 25 mM TrisHCl, pH 7.5/25 mM NaCl/5 mM $MgCl_2$/2% (vol/vol) Triton X-100/0.3 mg of heparin per ml/1 ug of trichodermin per ml/60 ug of phenylmethylsulfonyl fluoride per ml. Polysomes were isolated from the homogenate by $MgCl_2$ precipitation as described by Palmiter, *Biochemistry,* 13:3606–3615 (1974) (incorporated herein by reference), and stored at $-70°$. Twenty-five $A_{260}$ units of polysomes were obtained per gram of adrenal powder.

On linear sucrose gradients approximately 70% of the $A_{260}$ material sedimented as polysomes; the remaining absorbance was present in 80S monosomes. Polysomes (1,000 $A_{260}$ units) were clarified with a 10 minute centrifugation at 20,000 x g, then diluted to 15 $A_{260}$/ml in a buffer containing 25 mM Tris-HCl at pH 7.5, 150 mM NaCl, 5 mM $MgCl_2$ 0.1% Nonidet P-40, heparin at 0.2 mg/ml, and trichodermin at 1 ug/ml and incubated with 6.25 mg of anti-receptor IgG or non-immune IgG for 1 hour with stirring at 4° C.

The polysome/antibody slurry was then passed twice through a column of protein A-Sepharose (0.7×13 cm) equilibrated in the above dilution buffer at a flow rate of 8–10 ml/hour at 4° C. The column was washed overnight with 120 ml of dilution buffer. Bound polysomes were eluted at a maximal flow rate with 20 ml of 25 mM Tris-HCl, pH 7.5/20 mM EDTA. The eluted fraction was heated 5 minutes at 65° C., brought to 0.5 M NaCl and 0.2% $NaDodSO_4$ cooled to 24° C., and passed through a column of oligo(dT)cellulose (0.8×2.3 cm) equilibrated in 10 mM Tris-HCl, pH 7.5/0.5 M NaCl. The column was washed with 20 ml of this buffer and poly(A)+ RNA was eluted with 5 ml of 10 mM Tris-HCl, pH 7.5. Yeast carrier tRNA (50 ug) was added, and the RNA was precipitated twice with NaOAc and ethanol. This immunopurified poly(A)+ RNA was resuspended in 20 ul of water and stored at $-70°$ C.

The immunoselected poly(A)+ RNA was assayed for the presence of LDL receptor mRNA by in vitro translation in a reticulocyte lysate system. The lysate system is described as follows.

Aliquots of poly(A)+ mRNA were incubated with 2.5 mM $CH_3HgOH$ for 10 min at 4° C. and then translated in rabbit reticulocyte lysates prepared as described by Pelham and Jackson, *Eur. J. Biochem.,* 67:247–256 (1970), and supplemented with 80 mM KOAc, 1 mM $Mg(OAc)_2$, 19 amino acids (excluding methionine) at 16 uM each, and [$_{35}$S]methionine at 0.2 mCi/ml (1 $Ci=3.7\times10^{10}$ Bq) The final concentration of $CH_3HgOH$ in the translation reaction was 0.3 mM. Translation products were analyzed by electrophoresis on $NaDodSO_4$/7% polyacrylamide gels.

Total adrenal gland poly(A)+ RNA directed the synthesis of many proteins, as determined by $NaDodSO_4$ gel electrophoresis and fluorography of the synthesized products. Poly(A)+ RNA derived from the immunopurified polysomes directed synthesis of several of the same protein bands plus one clear addition: a protein that migrated with a $M_r$ of approximately 120,000. This protein was not demonstrable after translation of poly(A)+ RNA selected from polysomes with nonimmune IgG. Biosynthetic studies on the LDL receptor from hamsters and rabbits have shown that the receptor is initially made as an apparent 120,000 $M_r$ precursor (where $M_r$ stands for molecular weight in daltons) that undergoes a series of posttranslational glycosylation events during transport to the cell surface, resulting in a mature protein with an apparent $M_r$ of 160,000. Thus, the size of the enriched protein seen after translation of the immunoselected poly(A)+ RNA was consistent with that of the LDL receptor precursor.

Preparation and Screening of the Bovine cDNA Clone Bank

The immunoselected poly(A)+ RNA was used to construct a cDNA library by the method of Okayama and Berg, *Mol. Cell. Biol.,* 2:161–170 (1982) (incorporated herein by reference) from poly(A)+ RNA derived from 2,000 $A_{260}$ units of polysomes. In the cloning reactions, which employed enzymes obtained from Life Sciences and P-L Biochemicals, 1.4 ug of dT-tailed vector primer and 0.52 pmol of dG-tailed linker were used.

Portions of the cDNA library were used to transform Escherichia coli RR1 to ampicillin resistance by the $CaCl_2$-shock procedure described in Maniatis, et al.

*Molecular Cloning* (Cold Springs Harbor Laboratory, Cold Spring Harbor, N.Y., page 250), incorporated herein by reference. Colonies were plated at high density on nitrocellulose filters, and two replica filters were prepared for hybridization (Maniatis, supra, p. 316). To reduce nonspecific background, baked filters were washed overnight in 50 mM Tris-HCl, pH 8/1 mM EDTA/1 M NaCl/0.1% NaDodS04 at 37 or 42° C. and then incubated at 65° C. for 3 hr in 4×SSC (1×$SSC$=0.15 $M$ $NaCl$/15 $mM$ $sodium$ $citrate$), 10×Denhardt's solution (1X=0.02% polyvinylpyrrolidine/0.02% bovine serum albumin/0.02% Ficoll) (Maniatis, supra, p. 327), and sonicated and denatured E. coli DNA at 1000 ug/ml.

Hybridization was performed overnight in the latter solution containing $^{32}$P-5'-end-labeled oligonucleotide mixtures (6×10$^6$ cpm/pmol at 1 pmol/ml) prepared as described below. Hybridization temperature for a given oligonucleotide probe corresponded to the minimum melting temperature, $t_m$, calculated from the empirical formula $t_m = 2°$ $C. \times (number$ $of$ $dA$ $dT$ $bp) + 4°$ $C. \times (number$ $of$ $dG$ $dC$ $bp)$, in which bp is base pairs. Filters were washed three times in 4×SSC at the hybridization temperature for 30 minutes per wash, dried at room temperature, and subjected to autoradiography. Positive clones were picked from the master plate and purified through several rounds of screening.

The hybridization probes used in the screening protocol detailed above were prepared based on sequence information obtained from peptide subfragments of the LDL receptor protein as follows.

The purified LDL receptor was digested with CNBr, an internal CNBr fragment was isolated by high pressure liquid chromatography (HPLC), and its partial amino acid sequence was determined by automated Edman degradation. CNBr fragments were generated from two different preparations of reduced and [$^3$H]carboxymethylated receptor (1.6 and 1.8 mg of protein) and fractionated by reverse-phase HPLC on a Brownlee (Santa Clara, CA) RP 300 column. The CNBr peptide described here was subjected to two separate runs on an automated Beckman 890C sequencer using a 0.25 M Quadrol program and the nonprotein carrier Polybrene. Yields of the NH$_2$-terminal residue of the CNBr peptide were 400 and 1,100 pmol for the two runs. Repetitive yields, calculated on the basis of recovery of the phenylthiolhydantion of [$^3$H]cysteine, averaged 91%.

Two families of synthetic oligonucleotide probes that corresponded to all possible codons specifying the sequence of amino acids in two neighboring regions of this CNBr fragment were synthesized. One family of oligonucleotides, designated A in Table I consisted of 32 tetradecamers encoding (Met)-Ala-Glu-Asn-Leu. The existence of a methionine residue at the amino terminus of this sequence was inferred from the fact that the peptide was generated by CNBr digestion. A second family of tetradecamers, designated B and B* in Table I, encoded the sequence Pro-Glu-(Asp)-Ile-Val. The assignment of the Asp residue in this sequence was provisional because it was observed in only one of two sequenator runs. The B/B* oligonucleotide family consisted of a total of 48 members that were synthesized as two subfamilies of 24 each, differing only in the codons used to specify the Pro residue (CC$_T$ in B and CC$_G$ in B*).

TABLE I

CNBr Peptide Sequence and Oligonucleotide Synthesis

TABLE I-continued

| Met Ala Glu Asn Leu | Leu Ser Pro Glu (Asp) Ile Val |
|---|---|
| C             C | C              C |
| T       A  C  C | T    A    C  T |
| ATGGC  GA AA   T | CC  GA GA  AT GT |
| A    G   T T | A    G    T  A |
| G | G |
| Oligo Family A | Oligo Families B and B* |
| 32 × 14 mers | 2 × 24 × 14 mers |

Thirty hybridization positive cDNA clones were identified by screening the above cDNA library with oligonucleotide family B. When these clones were probed separately with the subfamilies B or B*, 16 clones hybridized strongly with oligonucleotide mixture B, but not with B*. Twelve of the 30 clones were positive only with mixture B*. These 28 positive clones were then screened with oligonucleotide mixture A, and two plasmids, both from the latter group of 12, hybridized with this probe. These two clones were considered to contain cDNAs for the receptor and were chosen for further study.

Plasmid DNAs from the two clones that hybridized to both the B* and A oligonucleotide probes were subjected to restriction endonuclease mapping, and the results indicated that these two clones were identical. Therefore, these clones were considered to be representative bovine LDL receptor cDNA clones. One of these clones, designated pLDLR-1, was chosen in order to confirm that it represented a true LDL receptor clone.

To confirm the identity of pLDLR-1, total poly(A)+ RNA was extracted from bovine adrenal glands and liver and analyzed in blotting experiments using nick-translated $^{32}$P-labeled plasmid as a probe. RNA blotting experiments were performed as follows. Total RNA was isolated by treatment of tissues or cells with guanidinium thiocyanate (Maniatis, supra, page 196). Poly(A).+ RNA was purified by oligo(dT)-cellulose chromatography, denatured with glyoxal, size-fractionated by electrophoresis (20 volts for 16 hours) on 1.5% agarose gels containing 40 mM 3-N-morpholinopropanesulfonic acid (pH 7.0), and then transferred to Zeta Probe membranes (Bio-Rad) by capillary blotting in 20 x SSC. Prehybridization and hybridization were carried out as described by Maniatis, supra, page 320.

Increasing amounts of adrenal gland RNA yielded a progressively stronger hybridization signal corresponding to a mRNA of approximately 5.5 kb. Densitometric scanning showed that the signal obtained with a given amount of adrenal RNA was 9-fold more intense than that obtained with the same amount of liver RNA. Previous studies have shown that functional LDL receptor activity is about one order of magnitude more abundant in bovine adrenal than in bovine liver, a finding that coincides with the difference in the abundance of the mRNAs discussed above.

The number of LDL receptors can be markedly reduced when cultured cells are grown in the presence of cholesterol or related sterols. Poly(A)+ RNA was isolated from human A-431 cells grown in the absence of sterols (receptor-induced) and presence of sterols (receptor-suppressed) and analyzed by blotting with pLDLR-1. A strong hybridization signal from a mRNA of approximately 5.5 kb was detected in the induced RNA and this signal was reduced by more than 90% in the suppressed RNA.

These results indicate that pLDLR-1 contains a cDNA copy of at least a portion of the bovine LDL receptor gene. This clone has been deposited as ATCC #39965. Fortunately, there is sufficient homology between the bovine receptor gene and the human gene to allow the use of the bovine sequence as a probe in isolating the human gene. These procedures are disclosed in Example II.

EXAMPLE II

Cloning and Characterization of the Human LDL Receptor Gene

The strategy used to obtain a full-length cDNA for the human LDL receptor is outlined in FIG. 1. The partial bovine cDNA (pLDLR-1) was used to screen a human genomic library cloned in bacteriophage lambda by the procedure of Lawn, et al., Cell, 15:1157–1174 (1978) (incorporated by reference herein) as follows. Approximately $1 \times 10^6$ bacteriophages containing human genomic DNA inserts were screened with $^{32}$P-labeled pLDLR1. Hybridization was performed under conditions of reduced stringency: 30% formamide, 5×SSC, 5×Denhardt's solution, 0.1% SDS (Sodium Dodecyl Sulfate), 100 ug/ml salmon sperm DNA and 1 ug/ml poly(A) at 42° C. Filters were washed twice at 22° C. for 10 minutes in 2 x SSC, 0.1% SDS (sodium dodecyl sulfate), and once at 54° C. for 60 minutes in the same solution.

From this human genomic clone library, a single clone, lambda h1, was identified. It contained an 11 kb (kilobase pair) insert encoding the 3' end of the human LDL receptor gene. Lambda h1 was used to generate a 236 bp Pvu II fragment that served as a unique probe for the COOH-terminal end of the human LDL receptor cDNA.

A cDNA library was constructed from human fetal adrenal poly(A)+ RNA by the method of Okayama and Berg, Mol. Cell. Biol., 2:161–170 (1982), incorporated herein by reference. In the cloning reactions, we used commercially obtained enzymes, 2 ug of poly (A)+ RNA, 1.5 ug of dT-tailed pcDV1 vector-primer, and 0.52 pmole of dG-tailed linker. Following transformation into E. coli HB101, plasmid cDNAs were isolated from approximately $3 \times 10^5$ transformants and enriched for longer cDNAs (6 to 10 kb) by the sublibrary method of Okayama and Berg, Mol. Cell. Biol., 3:280–289 (1983) incorporated herein by reference.

Human LDL receptor cDNAs were identified using two probes, a 5'-specific oligonucleotide family consisting of 32 heptadecamers derived from the sequence Asn-Glu-Phe-Glu-Cys-Gln, present at the NH2 terminus of the bovine LDL receptor protein and the 3'-specific 236 base pair Pvu II fragment containing a 158 bp COOH-terminal exon that was derived from the human genomic clone lambda h1 (described above). Oligonucleotides were synthesized by the phosphoramidite method and provided by Mark Zoller (Cold Spring Harbor Laboratory) and Ray MacDonald (University of Texas Health Science Center at Dallas). Replica filters were screened, and five colonies out of 2396 recombinants were positive with both the 5'- and 3'-specific probes. The plasmid with the longest cDNA insert in these positive clones (4.9 kb) was designated p101.

The nucleotide sequence of the cDNA insert of p101 revealed that it did not contain the 5' end of the coding region of the LDL receptor mRNA. Nucleotide sequence analysis of this cDNA revealed that the 5'-oligonucleotide probe was not hybridizing to the region corresponding to the extreme NH2 terminus of the protein. Rather, the probe was hybridizing to an imperfect repeat of the NH2-terminal sequence that occurred within the coding region. The open reading frame continued to the extreme 5' end of the cDNA insert in p101, and there was no evidence of a predicted signal sequence or an initiator methionine codon. Therefore, p101 did not contain the entire coding region.

To obtain the rest of the coding region, an oligonucleotide corresponding to a sequence near the 5' end of the cDNA insert in p101 was prepared and primer extension using human fetal adrenal poly(A)+ RNA as a template was performed. A synthetic oligonucleotide of 20 bases complementary to the mRNA strand and originating 63 nucleotides from the 5' end of the cDNA insert of p101 was used to construct a primer-extended cDNA library from human fetal adrenal poly(A)+ RNA in pBR322. This library was screened with a second oligonucleotide of 20 bases that originated 8 nucleotides from the 5' end of the cDNA insert of p101. Of the 1044 recombinants screened, one plasmid, designated p203, was identified whose cDNA insert overlapped that of p101 for 83 nucleotides and extended to near the approximate 5' end of the human LDL receptor mRNA.

Figure 2:
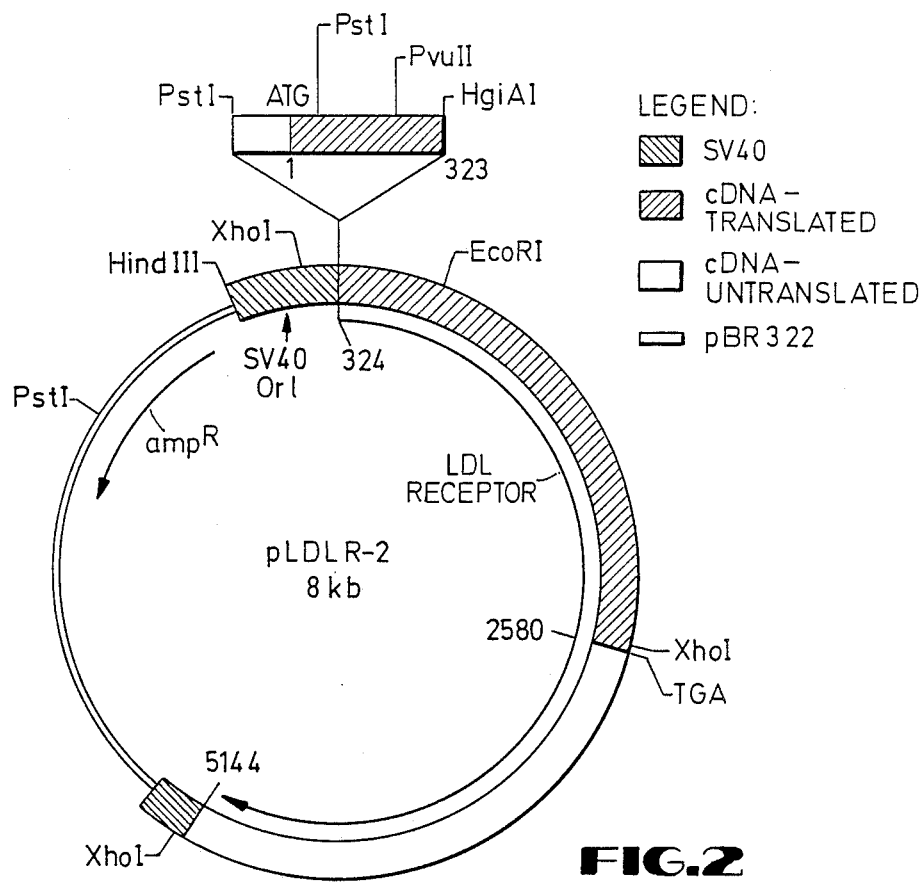
FIG. 2 is a structural representation of recombinant plasmid pLDLR-2 which contains a nearly full-length cDNA for the human LDL receptor gene. The coding region (hatched area) encompasses nucleotides 1 to 2580. This fusion plasmid was constructed by joining the cDNA inserts of p203 (nucleotides 1 to 323) and p101 (nucleotides 324 to 5144) via overlapping Hgi Al sites. The solid areas in pLDLR-2 denote regions in the cloning vector that contain SV40 sequences, including the origin of replication, 16S and 19S donor and acceptor splicing sites, and polyadenylation signals.

To construct a nearly full-length cDNA, it was necessary to ligate the appropriate portions of p101 and p203 (FIG. 2). Owing to a paucity of convenient restriction enzyme sites, this ligation required several partial digests and the preparation of two intermediate plasmids as follows.

A cDNA containing the entire translated region of the human LDL receptor mRNA, was constructed by joining the ineserts of p203 and p101 via overlapping Hgi Al sites (FIG. 2). The construction involved three partial digestions, three multifragment ligations, and two intermediate plasmids. p203 was partially digested with Pst 1 and then digested completely with Pvu II to yield a fragment of 341 bp. A Hind III-Pst 1 (518 bp) fragment was purified from pL 1, which contains the early region promoter and splicing signals of the SV40 virus (see FIG. 2 and Okayama and Berg, 1983). These two fragments were ligated and cloned into the Hind III-Pvu II site of pBR322. This intermediate plasmid was designated pHP1. A 394 bp Hgi AI-Eco R1 fragment from the 5' end of p101 was mixed with a 105 bp Pvu II-Hgi Al fragment from the 3' end of p203 and ligated into Eco R1-Pvu II-digested pBR322. This intermediate plasmid was designated pEP1. pEP1 was partially digested with Pvu II and then completely digested with Eco R1 to yield a 499 bp Pvu II-Eco R1 fragment. This DNA fragment was ligated with the 859 bp Hind III-Pvu II insert from pHP1 and with the 7 kb Hind III-Eco R1 fragment of p101 corresponding to the 3' eighty-five percent of the cDNA and the cloning vector. The final 8.4 kb plasmid designated pLDLR-2, contained a full-length cDNA copy of the human LDL receptor linked to SV40 sequences (FIG. 2).

The result of this genetic engineering was pLDLR-2, a plasmid containing a 5.3 kb cDNA insert corresponding to the entire coding region, the entire 3' untranslated region, and at least a portion of the 5' untranslated region of the human LDL receptor mRNA (ATCC #39966).

The cDNA insert of pLDLR-2 was sequenced by the method of Maxam and Gilbert, Meth. Enzymol., 65:499–500 (1980)and Sanger et al, *Proc. Natl. Acad. Sci. USA*, 74: 5463–5467 (1977), both of which are incorporated herein by reference. The nucleotide sequence determined for the human LDL receptor cDNA is displayed in FIG. 3 along with the predicted amino acid sequence of the corresponding receptor protein. On the 5' side of the 5' end of the sequence shown in FIG. 3, plasmid pLDLR-2 contains extraneous DNA that appeared to arise from the formation of a hairpin loop during the cloning reactions. The presence of this extraneous DNA in no way affects the utility of this cDNA for the diagnostic purposes outlined in this application.

EXAMPLE III

Isolation of GenomicRecombinant Clones Corresponding to the Normal LDL Receptor Gene Genomic clones spanning the 3' end of the human LDL receptor gene were isolated from a genomic library constructed in the bacteriophage vector, lambda Charon 4A. The library was provided us by T. Maniatis, Harvard University. Recombinant phage were screened with $^{32}$P-labeled pLDLR-1 and pLDLR-2, cDNA probes for the bovine and human LDL receptors (see Examples I and II, respectively). Hybridization was performed under stringent conditions: 50% formamide, 5×SSPE (1×*SSPE*=0.18 *M NaCl*/10 *mM NaH2PO4, pH* 7.4/2 *mM EDTA*), 5×Denhardt's solution , 0.1% SDS, 100 ug/ml salmon sperm DNA, and 1 ug/ml poly(A) at 42° for 16 hours. Filters were washed twice at 22° C. for 10 minutes in 2×SSC (1×*SSC*=0.15 *M NaCl*/0.015 *M sodium citrate*), 0.1% SDS and once at 60° C. for greater than or equal to 2 hours in 0.1×SSC and 0.1% SDS. Washed filters were air-dried and subjected to autoradiography at -70° C. with Kodak XAR-5 film and Dupont Cronex Lighting Plus Intensifying screens.

Figure 6:
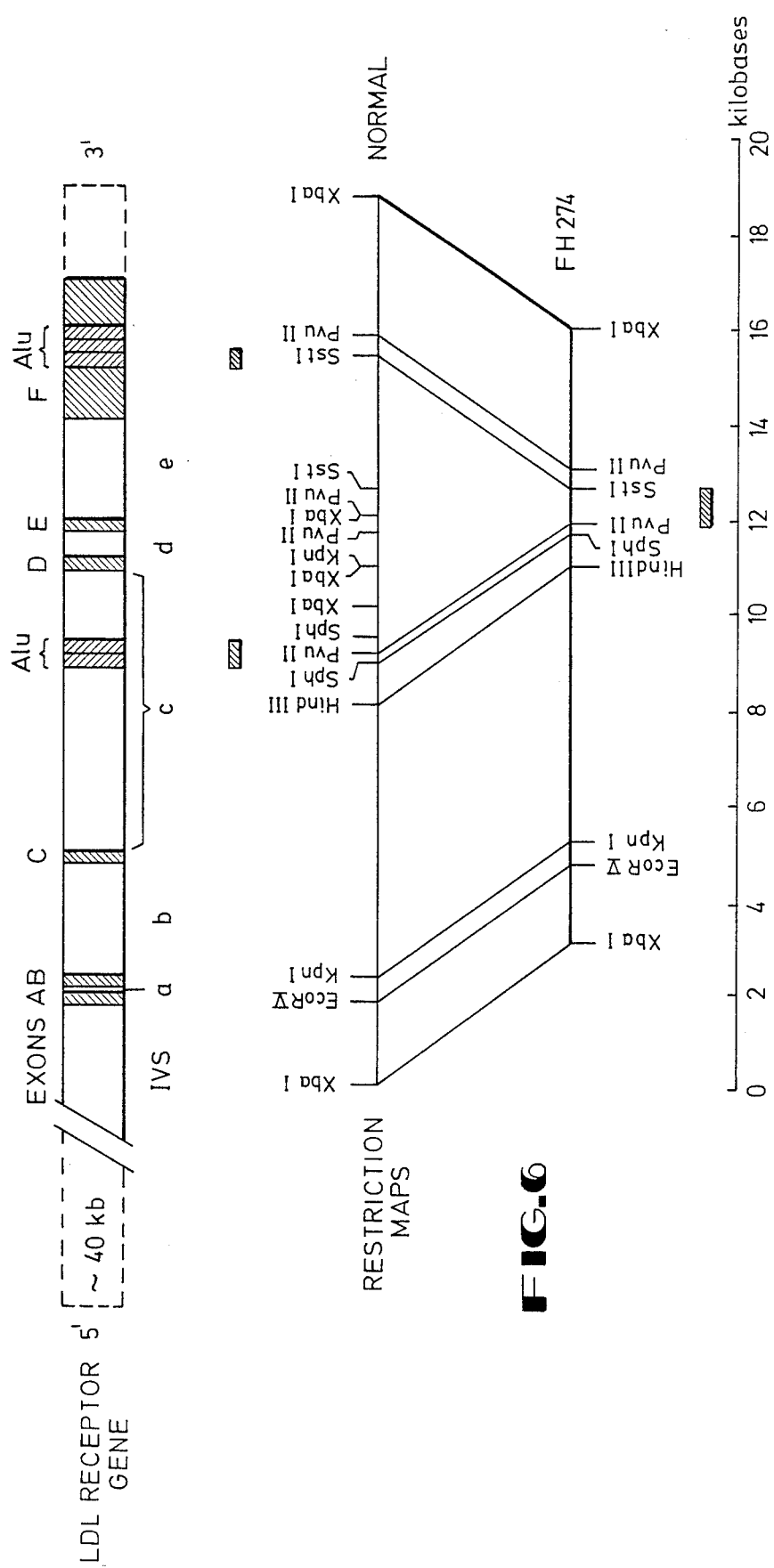
FIG. 6 is a comparison of restriction maps of the 3' end of the normal LDL receptor gene and the deletion-bearing gene from FH 274. The scale at the bottom indicates the length of genomic DNA in kilobases. The organization of the normal LDL receptor gene is shown in the diagram at the top. Exons are indicated by solid segments and upper case letters; intervening sequences (IVS) are indicated by open segments and lower case letters. The Alu repetitive sequences in IVS c and Exon F are indicated. Restriction enzyme recognition sites used to define the gene deletion in FH 274 are shown.

The 3' end of the normal LDL receptor gene shown in FIG. 6 is contained on three of the lambda clones isolated in the above manner: lambda 33-2, lambda 33-1, and lambda hl. Note that the restriction map of the normal LDL receptor gene shown in FIG. 6 also displays both "exons" and IVS regions (intervening sequences or "introns"). The term "exons" refers to domains of a gene that are "transcribed" into mRNA and eventually appear in the cytoplasm as mature mRNA. Any one gene may have numerous exons, which together, comprise the structural gene itself. Exons are separated within the gene by regions referred to as "intervening sequences" or IVS regions. The IVS regions are transcribed into the initial RNA transcript of the DNA. However, unlike exons, the IVS regions are processed out of the initial RNA transcript and are therefore never expressed in the ultimate protein product.

The DNA insert in lambda 33-2, approximately 12 kb, encodes Exons A, B, and C; the insert in lambda 33-1, approximately 11 kb, encodes Exons D, E, and F; and the insert in lambda hl, approximately 11 kb, encodes Exons E and F. The $^{32}$P-cDNA probes shown in FIG. 4A correspond to the following regions of the LDL receptor gene: probes 2-5 hybridize to exons in the 5' end of the LDL receptor gene denoted as approximately 40 kb of DNA in FIG. 6; probe 6 hybridizes to Exon C; probe 7 hybridizes to the 5' half of Exon F; and probes 8 and 9 both hybridize to the 3' half of Exon F. Exon C encodes the O-linked sugar region of the receptor (amino acid residues 693 to 749); Exon D encodes the region between the O-linked sugar domain and the membrane-spanning domain plus 8 of the 22 amino acids comprising the membrane-spanning domain (residues 750 to 775); Exon E encodes the remainder of the membrane-spanning domain and 39 of the 50 amino acids comprising the cytoplasmic domain (residues 776 to 828); Exon F encodes the terminal 11 amino acids of the cytoplasmic domain of the receptor protein residues 829 to 839) plus all of the 3' untranslated region of the mRNA.

EXAMPLE IV

Case Study of an Individual with Familial Hypercholesterolemia

The present example discloses the use of the recombinant clones disclosed in Example's II and III to characterize a mutation in the structural gene for the LDL receptor in a family with FH. The index case is a young man (B.H.), hereafter designated FH 274, who has all of the clinical features of homozygous FH. Previous functional studies revealed that cultured fibroblasts from FH 274 bound about one-third of the normal amount of $^{125}$I-labeled LDL. However, the receptors in FH 274 did not cluster in coated pits and hence did not transport their bound LDL into the cell. Thus, FH 274 was categorized functionally as an "internalization-defective" mutation. Studies of fibroblasts from the relatives of FH 274 revealed that he had inherited two different mutant alleles; the allele encoding the internalization-defective receptor was inherited from his mother and a null (or silent) allele that produced no functional receptor protein was inherited from his father.

Preliminary biosynthetic studies of cultured fibroblasts from FH 274 revealed that the LDL receptor protein encoded by the internalization-defective allele is about 10,000 daltons smaller than the normal receptor. Accordingly, a study of this mutation was initiated by analyzing the genomic DNA from FH 274 and his family members. As described below, we found that the mutant gene has undergone a large deletion that eliminates two exons completely and one exon partially.

The deletion mutation revealed by practice of the present invention with respect to FH 274 was shown to result from a recombination between two repetitive DNA elements: an Alu element in the intervening sequence (IVS) that precedes the exon encoding the membrane-spanning region of the receptor and an Alu element in the exon encoding the 3'-untranslated region of the gene. Alu sequences are human DNA sequences which display a highly repetitive character. It is thought that due to their highly repetitive nature, Alu sequences may be responsible for a number of genetic mutations: an Alu sequence from one region of a gene may cross-hybridize with Alu sequences from another region, forming a "loop" in the DNA. Thus, the deletion occurs when this "loop" is processed out of the gene, leaving an incomplete gene.

The resulting mutant gene, in the case of FH 274, produces a truncated LDL receptor that lacks a membrane-spanning region and a cytoplasmic domain. Most of these truncated receptors are secreted from the cell, but some of them remain associated with the outer surface of the cell. In this position they can bind LDL, but the lack of a cytoplasmic domain renders these receptors incapable of clustering into coated pits and carrying LDL into the cell.

Southern Blot Analysis of FH 274 DNA Relative to Normal DNA

The preferred mode contemplated by the present inventors for displaying a deletion mutation in an FH individual involves the use of a well-known technique known as Southern blotting. Briefly, Southern blotting is a procedure whereby genomic DNA from an individual is first isolated and fragmented into discrete fragments and separated electrophoretically on an agarose gel. The pattern of DNA from the gel may then be "imprinted" onto a stable matrix. The pattern of those fragments which correspond to the LDL receptor gene may then be visualized by hybridizing a labeled LDL receptor cDNA or genomic probe with the imprinted matrix and visualizing the gene pattern by means of the label.

In performing the initial DNA fragmentation, the DNA is preferrably restriction endonuclease digested into smaller DNA fragments. However, the only requirement is that the method chosen should be able to cleave the genomic DNA reproducibly into the same fragment pattern. In this manner, identically cleaved gene fragments will exhibit a reproducible pattern when separated, for instance, on the basis of fragment length. Thus, LDL receptor gene fragments from test individuals might be compared to the corresponding fragments from control individuals to detect a shift in the respective LDL gene pattern. A shift in the pattern of LDL receptor gene fragments from a test individual relative to a control pattern would be indicative of a mutation in the gene.

The present inventors have determined that the restriction endonuclease Xba I was capable of displaying the genetic mutation exhibited by FH 274. However, it is contemplated that in future case studies, it may become necessary to use other restriction enzymes. Thus, a battery of enzymes may be useful in certain instances to find the correct enzyme for that particular defect. Those of skill in the art will recognize that such a battery of digestions may be necessary.

After fragmenting the DNA, the fragments produced are then separated into a pattern whereby individual fragments are separated from one another. The preferable means for separating the DNA fragments is to separate the fragments according to size by subjecting the DNA to electrophoresis in an agarose gel matrix. Agarose gel electrophoresis is a procedure well-known in the art. However, other types of separation techniques may be used, including, for example, column chromatogarphy or density gradient centrifugation. The gel electrophoresis technique is useful in that it allows the separation of fragments in a manner which allows for precise determination of the apparent size of the separated fragments and allows for easy handling of the fragments so separated. Furthermore, the LDL receptor gene fragments which are present in the gel matrix may be directly visualized by the Southern blotting technique described more fully below.

FIG. 4B shows Southern blots of genomic DNA from normal cells and from FH 274, after digestion with Xba I, and hybridization with several cDNA probes. More particularly, the Southern blot hybridizations were performed as follows. Genomic DNA (4 ug) was isolated from cultured fibroblasts from the indicated subject (Maniatis, supra.), digested with XbaI (New England Biolabs), electrophoresed in 1% agarose containing buffer A (40 mM Tris-acetate, 3 mM $Na_2EDTA$, 20 mM NaOAc, and 18 mM NaCl at pH 8.15), and transferred to nitrocellulose paper by osmotic diffusion (Maniatis, supra). The paper was incubated for 16 hours at 42° C. with the appropriate $^{32}P$-labeled cDNA probe ($2-4\times10^6$ cpm/ml) in 50% formamide, 1% SDS, 5×Denhardt's solution, 5×SSPE, and 100 ug/ml E. coli DNA after prehybridization for 1 hour at 42° C. in the same solution without the $^{32}P$-labeled probe. After hybridization, the paper was washed in 1% SDS plus 2xSSC for 15 minutes at 23° C. and then in 1% SDS plus 0.1xSSC (for probe 1 hybridizations) or in 1% SDS plus 0.5xSSC (for probes 2-9) for 4 hours at 68° C. Filters were exposed to X-ray film with an intensifying screen for 24 hours at −70° C. Two representative blot hybridizations using probes 1 and 8 are shown in FIG. 4B.

The sizes and locations of $^{32}P$-labeled cDNA probes used to map the LDL receptor gene are shown in FIG. 4A by the closed bars and are numbered 1 to 9. Probe 1 (double-stranded DNA) was a mixture of a 2.1-kb EcoRI-SmaI fragment and three different 0.9-kb BamHI-XhoI fragments from p101, which together spanned most of the translated region of the gene. The fragments were purified by polyacrylamide gel electrophoresis and electroelution and then labeled with $^{32}P$ by random hexanucleotide priming as described by Feinberg and Vogelstein, *Analyt. Biochem*, 132:6-13 (1983), incorporated herein by reference. Probes 2 through 9 were prepared from M13 subclones of pLDLR-2 as a single-stranded, uniformly $^{32}P$-labeled DNA approximately 100 nucleotides in length by the method of Church and Gilbert, *Proc. Natl. Acad. Sci. USA*, 81:1991-1995 (1984), incorporated herein by reference. All probes had a specific radioactivity of at least $5\times10^8$ cpm/ug.

Briefly, to prepare probe 2 a DNA fragment encompassing nucleotides 267 to 1081 (FIG. 3) was cloned into the bacteriophage M13mp9 vector as described by Messing, *Meth. Enzymol.*, 101: 20-78 (1983), incorporated herein by reference. Single-stranded, uniformly $^{32}P$-labeled DNA probes approximately 100 bases long were prepared from the resulting clone by the method of Church and Gilbert, supra, using an M13 universal primer and the Klenow fragment of DNA polymerase I to extend the primer in the presence of three unlabeled deoxynucleotides and one alpha-$^{32}P$-labeled deoxynucleotide. The resulting radioactive primer extension product was denatured from the template by boiling, size-fractionated on a denaturing acrylamide gel, electroeluted, and then used directly as a probe. Probes 3-9 were prepared in a similar manner, except M13 clones containing different regions of the sequence in FIG. 3 were used as templates.

Figure 3D:
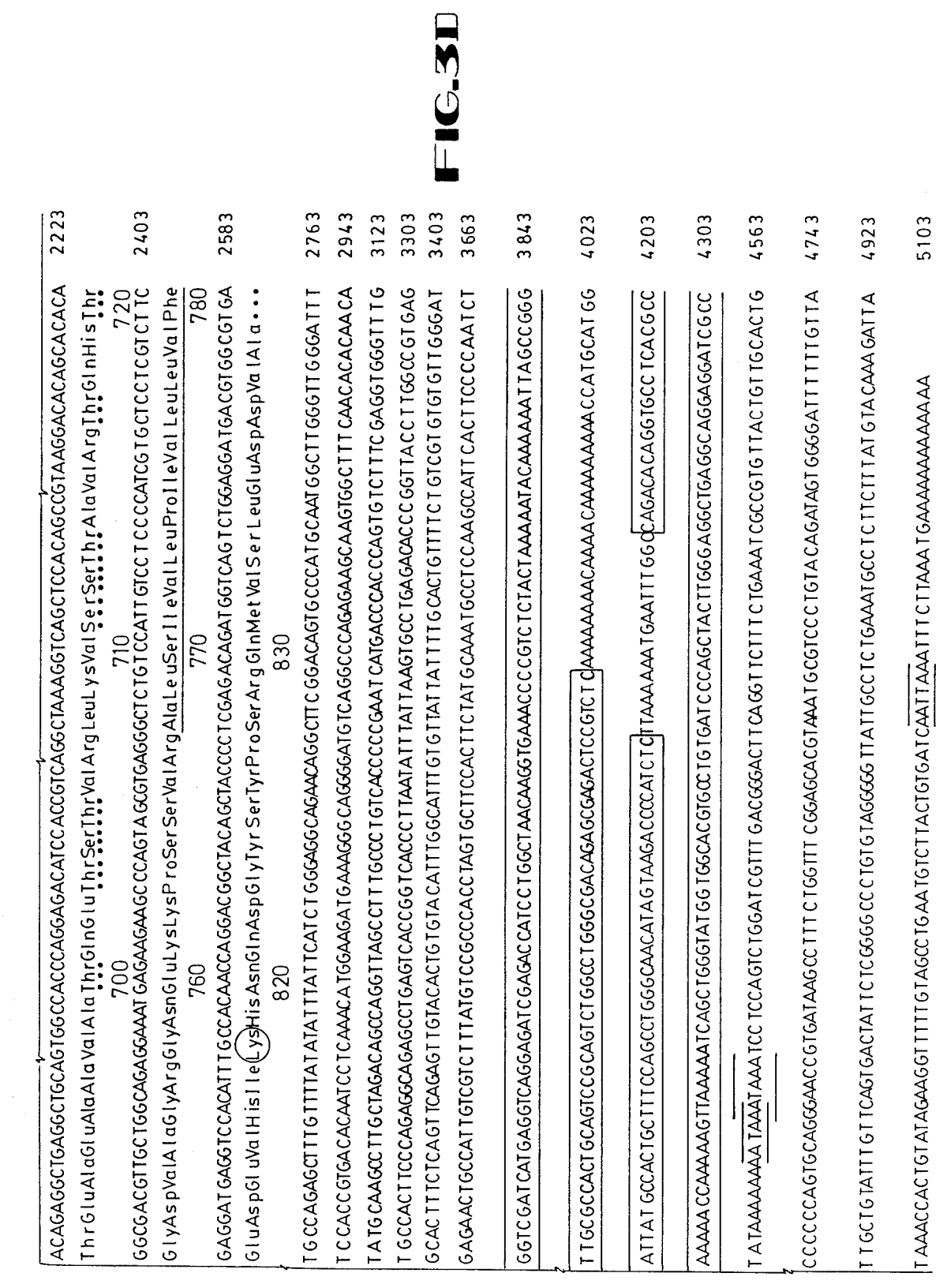

Referring to FIG. 3, probe 3 encompasses approximately nucleotides number 719 to 2544; Probe 4 encompasses approximately nucleotides 267 to 1078; Probe 5 encompasses approximately nucleotides 1573 to 3486; Probe 6 encompasses approximately nucleotides 2154 to 2544; Probe 7 encompasses approximately nucleotides 2545 to 3948; and Probes 8 and 9 encompass approximately 4508 to 4962.

FIG. 4B shows Southern blots of genomic DNA from normal cells and from FH 274 after digestion with XbaI and hybridization with several cDNA probes. Probe 1 was a mixture of cDNA fragments that spanned most of the translated region of the LDL receptor mRNA (FIG. 4A). When this probe was hybridized to the XbaI-digested genomic DNA from the normal subject, three bands were observed, of 23-, 10-, and 7-kb, designated A, C, and D, respectively (FIG. 4B). All of these normal bands plus one additional band of 13-kb, designated B, were present in the genomic DNA of FH 274. These findings suggest that one of the mutant alleles in FH 274 has a normal restriction pattern whereas the other allele gives rise to band B.

To localize the DNA segment that gives rise to band B, the XbaI digests were probed with short DNA fragments that corresponded to discrete regions of the LDL receptor cDNA (probes 2-9, FIG. 4A). Probes 2 to 5 hybridized to identical bands in normal and FH 274 DNA. Probes 6, 8 and 9 (but not probe 7) hybridized to the abnormal 13-kb band B in the FH 274 DNA. Inasmuch as band B does not hybridize with probe 7 but does hybridize with probes on either side of probe 7 (that is, probes 6, 8, and 9), this fragment appears to result from a deletion of DNA that includes the region encoding the mRNA encompassed by probe 7. This deletion would presumably involve the removal of at least one XbaI site with fusion of the adjacent DNA sequences into a single XbaI fragment of 13 kb, namely band B.

The specific mutation exhibited by FH 274 should in no way be construed as the only type of mutation that will be found in other FH individuals. Therefore, although probes 2 through 5 failed to demonstrate an altered LDL receptor gene fragment pattern in the case of FH 274, these probes will be useful in detecting other mutations in other FH individuals. Probes 2 through 5 hybridize to the 5' half of the receptor gene. Therefore, mutations which occur in this region of the receptor gene will be detectable using probes 2 through 5. Similarly, since probe 7 hybridizes to band D (FIG. 4A), it will be useful in detecting mutations which occur in this gene region.

Figure 5:
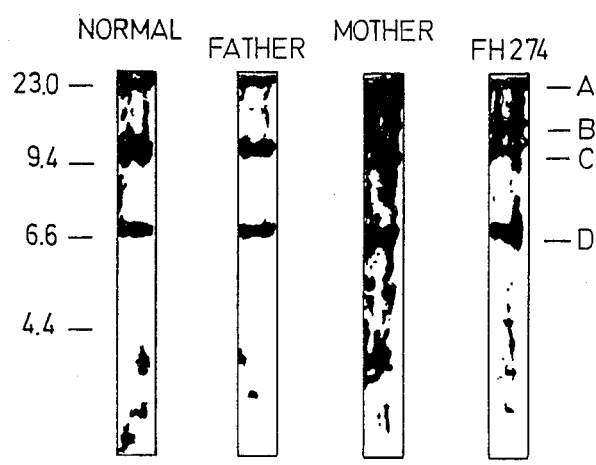
FIG. 5 is a Southern blot hybridization of XbaI-cleaved genomic DNA from a normal subject, FH 274 and his parents. Genomic DNA (5 ug) isolated from cultured fibroblasts from the indicated subject was digested with XbaI, electrophoresed, transferred to nitrocellulose, and hybridized with 32P-probe 1. The four relevant XbaI restriction fragments are designated A-D along the right side of the blot. Molecular size standards were generated by HindIII cleavage of bacteriophage DNA.

To determine whether band B originated from the maternal (internalization-defective) or paternal (null) allele, we performed XbaI digests of genomic DNA from the two parents. FIG. 5 shows that band B was present in the DNA from the mother, but not the father, indicating that the deletion was present on the internalization-defective allele.

Detailed Characterization of the Mutation Exhibited by FH 274

The following set of experiments demonstrate the utility of the present invention in being able to detect the presence of a mutation in the LDL receptor gene and in providing the means whereby such mutation may be specifically detailed and identified.

By using genomic recombinant clones and Southern blotting techniques with LDL receptor cDNA probes, a detailed restriction map of an FH individual can be generated. These gene mapping techniques are now wellknown to those of skill in the art. The particular map generated for FH 274 is displayed in FIG. 6. FIG. 6 is a comparison of restriction maps of the 3' end of the normal LDL receptor gene and the deletion-bearing gene from FH 274. The scale at the bottom indicates the length of genomic DNA in kilobases. The organization of the normal LDL receptor gene is shown in the diagram at the top. Exons are indicated by solid segments and upper case letters; intervening sequences (IVS) are indicated by open segments and lower case letters. The Alu repetitive sequences in IVS c and Exon F are indicated. Restriction enzyme recognition sites used to define the gene deletion in FH 274 are shown.

The restriction map of the normal receptor gene was generated from studies of three genomic clones (lambda 33-2, lambda 33-1, lambda h1) (Example III). The map of the gene in FH 274 was generated from lambda FH 274-10, which contains XbaI fragment B (FIGS. 4B and 5) (see below). Solid bars above or below the restriction maps denote segments of the normal and mutant genes that were used for DNA sequencing.

To obtain lambda FH 274-10, we prepared 570 ug of genomic DNA from fibroblasts of FH 274 and digested it with 1700 units XbaI. The digested DNA was extracted with phenol/chloroform and then chloroform, precipitated with 70% ethanol and 86 mM sodium acetate, and dissolved in 200 ul of buffer B (10 mM Tris-chloride and 1 mM $Na_2EDTA$ at pH 7.5). The DNA (80 ug) was redigested with 100 units XbaI, loaded onto a 1% low-gelling temperature agarose gel (Bethesda Research Laboratories) containing buffer A, and electrophoresed at 40 V for 72 hr at 4° C. After electrophoresis, ten 2-mm slices of the gel containing DNA fragments ranging from 9 to 23 kb were extracted, concentrated, and dissolved in 20 ul of buffer B. One aliquot (4 ul) of each DNA fraction, 5 ug of XbaI-digested genomic DNA from FH 274, and size marker fragments were loaded onto individual lanes of a 0.8% agarose gel containing buffer A and electrophoresed at 35 V for 16 hours at 23° C.

The DNA was transferred to nitrocellulose paper and hybridized with $^{32}P$-labeled probe 1 as described above. The resulting autoradiogram identified the fraction that contained the abnormal 13-kb XbaI fragment (fragment B, FIG. 4). The remaining DNA from this fraction (100 ng) was mixed with 500 ng of XbaI-digested arms of lambda Charon 35 and incubated with 490 units of T4 DNA ligase (New England Biolabs) for 72 hours at 14° C. The ligated material was packaged into lambda phage particles in vitro (Amersham) to yield a total of $6.7 \times 10^3$ plaque forming units. This library was screened with $^{32}P$-labeled probe 8 (FIG. 1), which was expected to detect only the abnormal fragment (13 kb), since the corresponding normal fragment (7 kb) was too small to generate viable recombinant phage. One recombinant clone was identified (lambda FH 274- 10) and isolated after an additional cycle of plaque purification. The 13-kb insert in lambda FH 274-10 was isolated from purified DNA, subcloned into pSP65 (Promega Biotec), and used for restriction endonuclease mapping.

FIG. 6 demonstrates that the PvuII site in IVSc and the SstI site in Exon F were separated by approximately 5.9-kb in the cloned fragments of the normal gene but only by approximately 0.6-kb in the cloned fragment of the FH 274 gene. Moreover, several restriction enzyme sites between the PvuII site and the SstI site are shown to be missing from the cloned FH 274 gene. These data confirmed the diagnosis made from the genomic Southern blots discussed above and further suggested that 5 kb of DNA was deleted from the FH 274 gene. The deletion included the 3' end of IVS c, all of Exons D and E and the IVS's separating them, and the 5' end of Exon F.

To locate precisely the 5' and 3' breakpoints and the structure at the deletion joint in FH 274, we determined the nucleotide sequences of the cloned portions of the genes delimited by the bars in FIG. 6. These sequences revealed that the deletion joint occurred between two repetitive elements of the Alu family that were oriented in opposite directions. The 5' side of the deletion joint was derived from an Alu sequence in IVS c. The 3' side of the deletion joint was derived from an oppositely-oriented Alu sequence in Exon F.

A test performed on a second FH individual using the present invention failed to reveal a deletion in the LDL receptor gene of that individual. It is felt that the defect in the LDL receptor gene of this individual is due to a point mutation. Defects which are not due to a deletion mutation can be detected by modification and extentions of the present invention which will be described in future applications.

Although recombination between repetitive DNA sequences has been postulated to be a cause of deletions, to the knowledge of the present inventors such rearrangements have not previously been reported in eukaryotic cells. In the most well characterized set of mammalian deletion mutations, i.e., those that occur in the human alpha- and beta-globin genes, one of the deletion breakpoints frequently occurs within an Alu sequence but the other breakpoint thus far has always occurred in a nonrepetitive sequence of DNA.

EXAMPLE V

Exon Mapping of Normal LDL Receptor Gene

The restriction enzyme map for the human LDL receptor gene was further extended in a 5' direction (relative to the map for the 3' end portion of the gene displayed in FIG. 6) through the mapping of overlapping bacteriophage lambda and cosmid clones which contained portions of the normal gene. In particular, pLDLR-2, which contains the coding sequence (cDNA) for the LDL receptor protein, was used to further screen both the charon 4A human clone bank (see Example III) and a human "cosmid" clone bank (discussed below).

Using routine gene restriction mapping techniques, an almost full-length genomic map of the normal LDL receptor gene was generated (see Sudhof et al. (1985), *Science*, 228: 815–822). The map, displayed in FIG. 7, demonstrates that the gene is more than 45 kilobases in length and contains 18 exons, most of which correlate with functional domains of the receptor protein. Thirteen of the 18 exons were found to encode protein sequences that are homologous to sequences in other proteins: five of these exons encode a sequence similar to one in the C9 component of complement; three exons encode a sequence similar to a repeat sequence in he precursor for epidermal growth factor (EGF) and in three protein of the blood clotting system (factor IX, factor X, and protein C); and five other exons encode nonrepeated sequences that are shared only with the EGF precursor. The LDL receptor thus appears to be a mosaic protein built up of exons shared with different proteins, and it therefore belongs to several supergene families.

Figure 7:
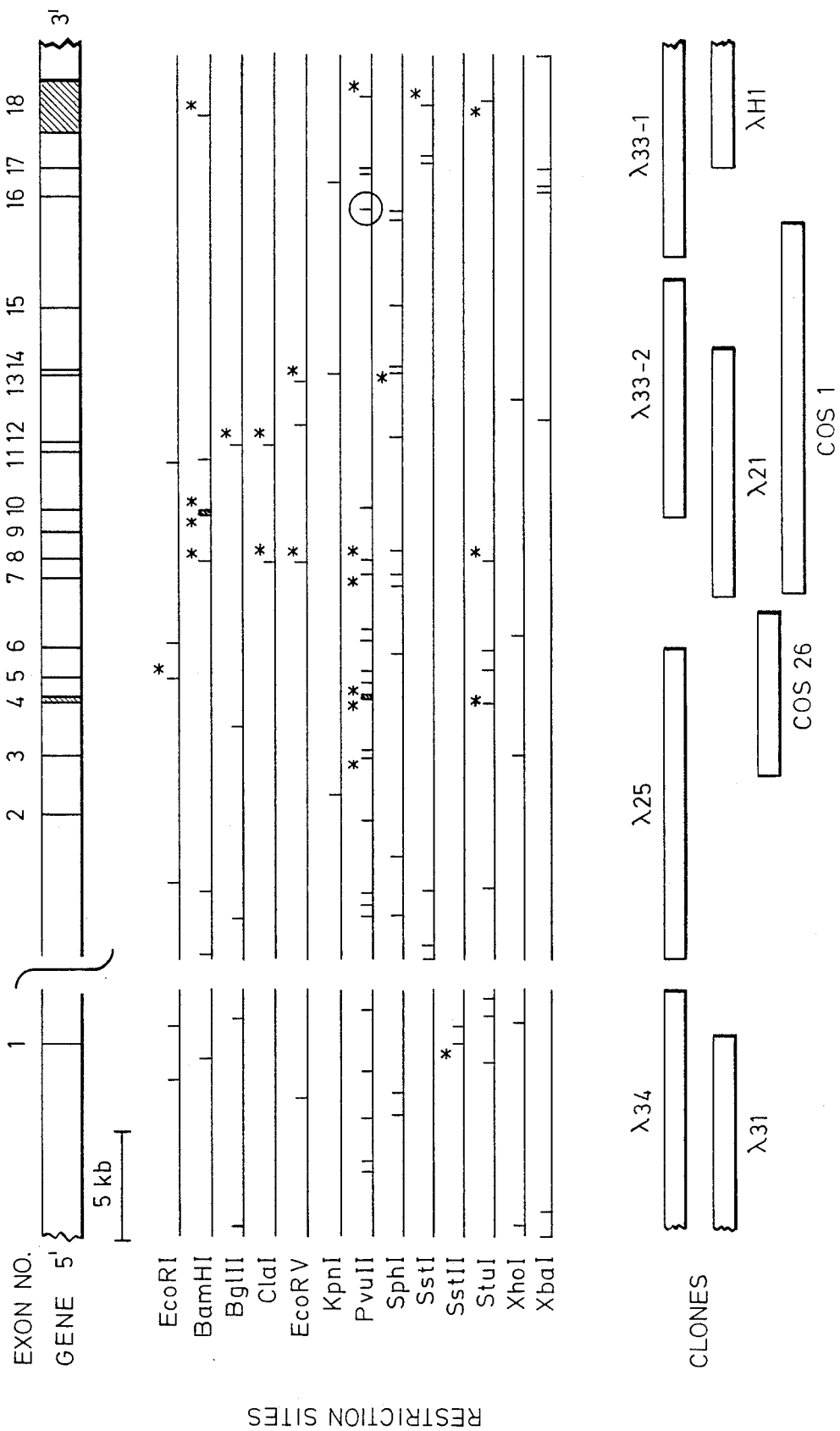
FIG. 7 is a map of the human LDL receptor gene. The gene is shown in the 5' to 3' orientation at the top of the diagram and is drawn to scale. Exons are denoted by filled-in areas, and introns by open areas. The regions encompassed by genomic DNA inserts in the seven bacteriophage lambda and two cosmid clones are indicated at the bottom. Cleavage sites for 13 selected restriction endonucleases are shown. Asterisks denote sites that are present in the cDNA. The encircled Pvu II site is polymorphic in human populations. The diagonal line between exons 1 and 2 represents a gap of unknown size not present in any of the genomic clones. Additional cleavage sites for the restriction enzymes shown may be present in this gap and in intron 6. The restriction map was verified by comparing overlapping and independently isolated genomic clones and by Southern blotting analysis of genomic DNA isolated from normal individuals.

Referring in particular to FIG. 7 is shown the map of the human LDL receptor gene. The gene is shown in the 5' to 3' orientation at the top of the diagram and is drawn to scale. Exons are denoted by filled-in areas, and introns by open areas. The regions encompassed by genomic DNA inserts in the seven bacteriophage lambda and two cosmid clones are indicated at the bottom. Cleavage sites for 13 selected restriction endonucleases are shown. Asterisks denote sites that are present in the cDNA. The encircled Pvu II site is polymorphic in human populations. The diagonal line between exons 1 and 2 represents a gap of unknown size not present in any of the genomic clones. Additional cleavage sites for the restriction enzymes shown may be present in this gap and in intron 6.

The lambda clones were isolated from $1.2 \times 10^7$ plaques of the human genomic bacteriophage lambda library. Cos1 was isolated from $6 \times 10^6$ colonies of a human cosmid library (Law et al. (1983), *Proc. Natl. Acad. Sci.*, 80: 5225). Cos26 was isolated from $0.9 \times 10^6$ colonies of a human cosmid library (Grosveld et al. (1982), *Nucl. Acids Res.*, 10: 0715). The libraries were screened with $^{32}$P-labeled probes derived from the human LDL receptor cDNA, pLDLR-2 (Yamamoto (1984), *Cell*, 39: 27). Probes were isotopically labeled by nick translation (T. Maniatis, E. F. Fritsch, J. Sambrook. Molecular Cloning: A Laboratory Manual (cold Springs Harbor Laboratory, Cold Springs Harbor, N.Y., 1982), 1: 545) or hexanucleotide priming (Feinberg et al. (1983) *Anal. Biochem.*, 132:6) and screening was carried out with standard procedures. Positive clones were plaque-purified or isolated as single colonies.

Thirty fragments from the nine genomic clones were subcloned into pBR322 and characterized by restriction endonuclease digestion, Southern blotting, and DNA sequencing of exon-intron junctions. The restriction map was verified by comparing overlapping and independently isolated genomic clones and by Southern blotting analysis of genomic DNA isolated from normal individuals.

As will be appreciated by those of skill when comparing the map displayed in FIG. 7 to the one in FIG. 6, the exons A-F of FIG. 6 correspond to exons 13–18 in FIG. 7. Therefore, to accommodate the additional 12 exons discovered in the 5' region of the gene, the exons were relabeled using a "numbering" system in place of a "lettering" system. By sequence comparison and by functional studies it is known that no exons exist in the gap region (diagonal line in FIG. 7) for which no overlapping clones have been isolated.

EXAMPLE VI

Mapping of FH 626-A Deletion Mutation Involving Exon 4

Patient FH 626 is a subject with the clinical phenotype of homozygous FH. Studies have shown that patient FH 626 inherited two different mutant alleles at the LDL receptor locus. From his father he inherited an allele that produces a receptor precursor with a decreased apparent molecular weight of 100,000 on SDS gels (20 kDa smaller than the normal precursor). Upon processing of carbohydrate, this mutant receptor increases to an apparent molecular weight of 140,000, which is still about 20 kDa smaller than the normal mature receptor. This shortened receptor appears on the cell surface, where it binds monoclonal antibody IgG-C7 ( a monoclonal antibody which is specific for the N-terminus of the LDL receptor), but fails to bind LDL. From his mother, patient FH 626 inherited a gene that produces a receptor precursor with a normal apparent molecular weight of 120,000. This mutant receptor never undergoes carbohydrate processing and does not appear on the cell surface. The only receptors expressed on the surface of the FH 626 cells are the ones produced by the paternal allele, i.e. the receptors that fail to bind LDL.

The binding-defective phenotype has been traced to a deletion of a single exon encoding one cysteine-rich repeat sequence. The surprising finding has been made that, whereas this mutant receptor fails to bind LDL, it retains some ability to bind B-VLDL. Thus, deletion of a single cystein-rich binding repeat can change the binding specificity of the LDL receptor.

The present example is directed to diagnostic techniques applicable in general to the detection of genetic FH mutations, and found to be particularly useful in identifying the type of mutation exhibited by FH 626, a deletion of exon 5 and neighboring sequences. Two basic approaches to the diagnostic method were applied, the Southern blot technique in accordance with the previous examples, and a method commonly referred to as Sl nuclease mapping, a technique found to be particularly suited to the identification of FH deletion mutations.

A. Southern Blotting of FH 626 DNA

With respect to the Southern blot approach to the diagnosis of FH mutations, all that is necessary is to identify an enzyme which will release a DNA fragment from the patient's DNA, wherein the restriction fragment spans the affected region. By comparing the size of the fragment identified as carrying the mutation, to the corresponding fragment from a normal FH gene, one can characterize the particular mutation, both in terms of type (i.e.-deletion or insertion) and the length of insertions or deletion. Although the comparative use of certain restriction enzymes are to be preferred for detailed mapping purposes, virtually any restriction enzyme which releases a mutation-carrying fragment, or which recognizes a site within the affected gene sequence(s), will provide for diagnostic utility.

To identify such an enzyme in the case of a previously uncharacterized mutation, one would initially simply perform a panel of restriction enzyme digestions on the patient and control DNA samples using all of the enzymes known to cleave within the LDL receptor gene. Such a panel would typically include but not be limited to, for example, the enzymes Eco RI, Asp 718, Taq I, Bam HI, Xba I, Hinf I, Bgl II, Cla I, Eco RV, Kpn I, Pvu II, Sph I, Sst I, Sst II, Stu.I, Xho I, Nde I, and Nsi I. An enzyme which specifically reveals the mutation (ie—a difference in the LDL restriction pattern for normal versus patient DNA) can thus be identified following specific visualization of the LDL receptor gene fragments by Southern blot hybridization using, for example, pLDLR-2 as probe.

With respect to FH 626 in particular, genomic DNA was isolated from the white blood cells of a normal individual and from the fibroblasts of FH 626, his mother, and his father. The isolated DNA was cut with the restriction endonuclease EcoRI, size-fractionated by electrophoresis on an agarose gel, and transferred to a nitrocellulose filter for Southern blotting. The filter was probed with an M13-derived, single-stranded $^{32}$P-labeled cDNA probe extending from the EcoRI site in exon 5 through exon 7 of the LDL receptor gene (FIG. 7). This probe was constructed starting with the cDNA insert of pLDLR-2, wherein the selected region corresponding to the transcribed gene sequences extending from exon 5 through 7. However, as those of skill will appreciate, the entire pLDLR-2 sequence could be used as a probe with equally good results.

Upon digestion of DNA from a normal individual, this probe detected two bands with approximate size of 8.5 and 1.8 kb (fragments B and C, respectively in FIG. 8). As shown at the bottom of FIG. 8, fragment C extends from the EcoRI site in exon 5 to an EcoRI site in intron 6. Fragment B encompasses DNA between EcoRI sites in intron 6 and intron 10. DNA isolated from the mother of FH 626 showed a normal EcoRI restriction pattern (FIG. 8). However, DNA isolated from FH 626 and his father both showed three EcoRI bands. Two of these fragments (B and C) correspond to those seen in normal individuals. The novel band (A) is approximately 13 kb in length. The amount of band C in the father and FH 626 DNAs appears to be reduced by half when compared with the normal or maternal DNA. Further restriction mapping suggested that band A arises from the deletion of an EcoRI site in exon 5 (FIG. 8, lower).

Inasmuch as the father is known to be the source of the binding-defective receptor that migrates at 140 kDa, the data of FIG. 8 assign that phenotype to the allele that lacks the EcoRI site. This paternal allele is referred to as the FH 626-a allele. From his mother, FH 626 inherited an allele that has a normal restriction pattern on Southern digests. This allele produces a receptor that remains at 120 kDa and is not processed to the mature form. This allele has been designated as the FH 626-b allele.

Referring in particular to FIG. 8 is shown a Southern blot hybridization of genomic DNA isolated from patient FH 626 and his parents. Genomic DNA (5 ug) from the indicated individual was subjected to two sequential digestions with a 5-fold excess of EcoRI. The DNA was subjected to electrophoresis on a 0.8% agarose gel, transferred to nitrocellulose, and hybridized at 42° C. for 16 h with a single-stranded $^{32}$P-labeled cDNA probe ($>10^9$ cpm/ug) containing the sequence encoded by exons 5 through 7 of the normal LDL receptor gene ($5 \times 10^9$ cpm/mM, 50% (v/v) formamide, 0.05% (w/v) each of bovine serum albumin, Ficoll 400, and polyvinyl pyrollidone 360, 5 x SSPE (1×SSPE is 0.18 M sodium chloride, 10 mM sodium phosphate, and 1 mM EDTA at H 7.4), 1% SDS, and 100 ug/ml of denatured and sonicated salmon sperm DNA). Following hybridization, the filter was washed at 68° C. for 4 h in 0.1×SSC (1×SSC is 0.15 M sodium chloride and 15 mM sodium citrate) and 1% SDS, dried, and used to expose Kodak XAR-5 film for 36 h at −70° C. with an intensifying screen. The positions to which HindIII fragments of bacteriophage lambda DNA migrated and their sizes in kilobases are indicated on the left side of the figures.

In the autoradiogram, band A contains exons 2, 3, 4, and 6; band B contains exons 7 through 10; and band C includes exons 5 and 6. An EcoRI restriction map of the LDL receptor gene in the region of exons 2 through 11 is shown below the autoradiogram. The asterisk (*) in the normal gene denotes the position of the EcoRI site that is missing in the deletion-bearing FH 626-a allele and the 5' start site of the $^{32}$P-labeled probe that was used in the experiment.

Figure 10:
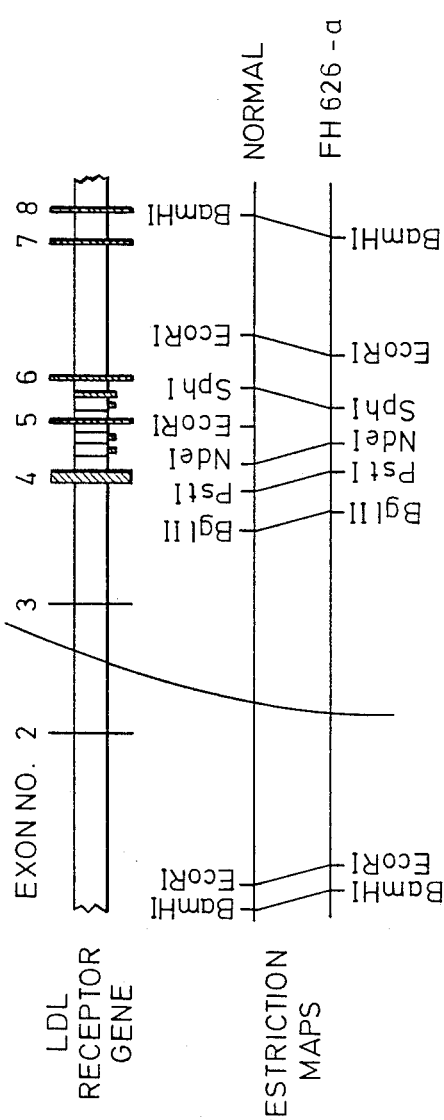
FIG. 10 is a restriction endonuclease map of the 5' end of the normal LDL receptor gene and the FH 626-a deletion-bearing allele. Exons are indicated by solid bars and introns by the connecting open segments in the schematic at he top of the figure. The positions of known Alu sequences, indicated by stripes, are shown in the intervening sequences. The orientations of the Alu repeats are indicated by arrows below the gene schematic. The restriction map of the FH 626-a allele harboring the deletion was determined using a pBR322 subclone.

Molecular cloning of the FH 626-a gene, followed by restriction enzyme mapping, revealed that the defect involved a deletion of exon 5 and neighboring sequences (see FIG. 9). As noted above, diagnosis of such a mutation through Southern blotting can be achieved with virtually any enzyme which may release an affected fragment or which cleaves within the affected region. However, certain enzymes have proven to be of particular usefulness in this regard, as demonstrated by the restriction map of FIG. 10. Demonstrated therein is a partial listing of enzymes which produce mutated fragments from the afflicted individual. For example, the enzymes, Bam HI, Eco RI, Bgl II, Pst I, Nde I, and Sph I will produce a distinctly different pattern of LDL gene fractionation in the normal as compared to the afflicted individual. However, as will be appreciated, these are by no means the only useful enzymes in this regard.

B. S1 Nuclease Mapping

S1 nuclease mapping represents an additional diagnostic method which is applicable to the diagnosis of deletion mutations. In general terms, the method involves the hybridization of total RNA from the test individual with an antisense radiolabeled single strand DNA probe (i.e.—non-coding strand probe) which corresponds to normal gene sequences surrounding the affected gene region. Following the formation of an RNA-DNA hybrid in the foregoing manner, the hybrid is subjected to an enzyme which specifically degrades single stranded regions of the hybrid (e.g.—S1 nuclease). Therefore, if perfect complementarily exists between the patient's RNA and the DNA probe, then no single stranded regions will exist in the hybrid duplex, and thus no digestion of the DNA probe will be observed.

However, as in the case of a gene deletion mutation, the deletion mutation will be expressed in the patients RNA molecules in that such RNA molecules will not contain the deletion sequences. Therefore, upon hybridization of deletion-carrying RNA with a selected DNA probe, the resultant duplex will not contain a one-on-one correspondence between RNA and DNA strands. In this case, regions of the duplexed DNA probe will be single-stranded and thus subject to single-strand-specific nuclease degradation. Therefore, the DNA probe will be fragmented, in the case of a deletion mutation, or left intact, where no deletion mutation is expressed in the RNA.

To demonstrate the utility of this S1 nuclease approach to the diagnosis of deletion mutations, S1 nuclease mapping was initiated with FH 626 RNA. The method employed was a modification of the method of Berk et al. ((1977), *Cell,* 12: 721-732). In general, the method involved the preparation of uniformly $^{32}P$-labeled, single-stranded, antisense probes encompassing different regions of the human LDL receptor mRNA and prepared from bacteriophage M13 DNA subclones by the method of Church and Gilbert ((1984) *Proc. Natl. Acad. Sci.,* 81: 1991-1995). Total RNA was isolated from cultured fibroblasts by the guanidinium isothiocyanate/CsCl procedure (Glisin et al. (1974), *Biochemistry,* 13: 2633). Hybridization was carried out in 25 ul of buffer containing 80% (v/v) formamide, 400 mM NaCl, 5 mM EDTA, and 40 mM PIPES (pH 6.4) for 16 h at 39° C. $S_l$ nuclease (700 units) was added to the hybridization mixture in 0.5 ml of buffer containing 250 mM NaCl, 30 mM KOAc (pH 4.5), 1 mM $ZnCl_2$ and 5% (v/v) glycerol, and the incubation was continued for 1 h at 37° V. Nuclease-resistant RNA-DNA hybrids were precipitated in ethanol together with 1 ug of carrier DNA, resuspended in formamide, boiled, and applied to denaturing polyacrylamide gels. After electrophoresis, gels were fixed with trichloroacetic acid, dried, and used to expose Kodak XAR-5 film with DuPont intensifying screens.

With respect to FH 626 in particular, the method employed total RNA from normal (control) cells (10 ug) or from FH 626 cells (20 ug) which was hybridized to a $^{32}P$-labeled single-stranded cDNA probe corresponding to nucleotides 422-1007 of the normal LDL receptor cDNA, after which the RNA-DNA hybrids were digested with 700 units of S1 nuclease as described in the preceding paragraph. Following electrophoresis of the Sl-resistant hybrids, the dried gel was used to expose Kodak XAR-5 film in the presence of an intensifying screen for 24 h at −70° C. Radiolabeled standards were derived from an MspI digest of pBR322. A schematic illustrating the results obtained in the experiment is shown below the autoradiogram in FIG. 11.

Referring now to FIG. 11 is shown the results of the S1 nuclease mapping of FH 626. As will be appreciated from viewing the autoradiogram (upper portion of FIG. 11), the radioactive DNA probe was capable of forming a continuous duplex with the normal RNA (center lane), and was thus "protected" from S1 nuclease cleavage. However, the same probe, when hybridized with FH 626 RNA, was incapable of forming a continuous duplex with RNA derived from the paternal allele, and was therefore partially degraded to smaller-sized fragments (releasing predominantly fragments of 273 and 190 nucleotides in length).

EXAMPLE VII

Mapping of FH 381 - A Deletion Mutation Involving Exon 17

The most common class of mutant FH alleles are those which produce no immunologically detectable LDL receptors--the so-called "null" allele. These account for approximately half of all mutations in the LDL receptor. It is likely that the null alleles represent a collection of many different mutations. Up to this point, however, none of the null phenotypes has been elucidated at the DNA level.

In the present example, the molecular basis of a deletion that produces a null phenotype at the LDL receptor locus is characterized. The mutant allele was isolated from an FH heterozygote, who is the mother of a compound heterozygote known as J.D. Previous biochemical studies have shown that J.D.'s mother has a null allele at the LDL receptor locus, which she transmitted to J.D. From his father, J.D. inherited an allele that encodes a receptor that cannot carry LDL into the cell, producing an internalization-defective phenotype. This internalization-defective phenotype was due to the substitution of a cysteine codon for a tyrosine codon in the cytoplasmic domain of the receptor. Here, the null phenotype produced by J.D.'s maternal allele is demonstrated to stem from a 5-kb deletion. Like a previously described deletion in the LDL receptor (see Example IV), the deletion in J.D.'s maternal allele begins in an Alu sequence in intron 15 (referred to as Exon C in FIG. 6). However, instead of recombining with a downstream sequence, this Alu sequence has been joined to an upstream sequence in exon 13. Surprisingly, there is a stretch of complementarity between the Alu sequence and the coding sequence in exon 13, thus allowing a double stem-loop structure to be drawn. This finding raises the general possibility that double stem-loop structures may predispose to deletions in the human genome.

Referring now to FIG. 12 is shown a Southern blot of a BamHI digest of genomic DNA from patient J.D. (FH 381), his father (FH 382), and a normal subject. The nitrocellulose filter was probed with a $^{32}P$-labeled cDNA fragment encompassing exons 3 through 18 of the LDL receptor gene. The normal DNA shows two BamHI fragments of 17 and 16 kb, designated A and B, respectively. The FH 380 DNA (from patient J.D.) shows an additional band of 12 kb, designated C. The abnormal 12-kb restriction fragment was inherited from the mother (FH 381). The DNA from the father showed a normal BamHI pattern. The father is known from biochemical studies to be the donor of the internalization-defective allele, and the mother is the donor of the null allele. The Southern digests indicate therefore that the gene encoding the internalization-defective allele has a normal BamHI digestion pattern, whereas the gene encoding the null allele gives rise to the abnormal 12-kb BamHI fragment. This difference in size made it possible to isolate this portion of the null allele from the mother's DNA (FH 381) by cloning in bacteriophage lambda.

Figure 13:
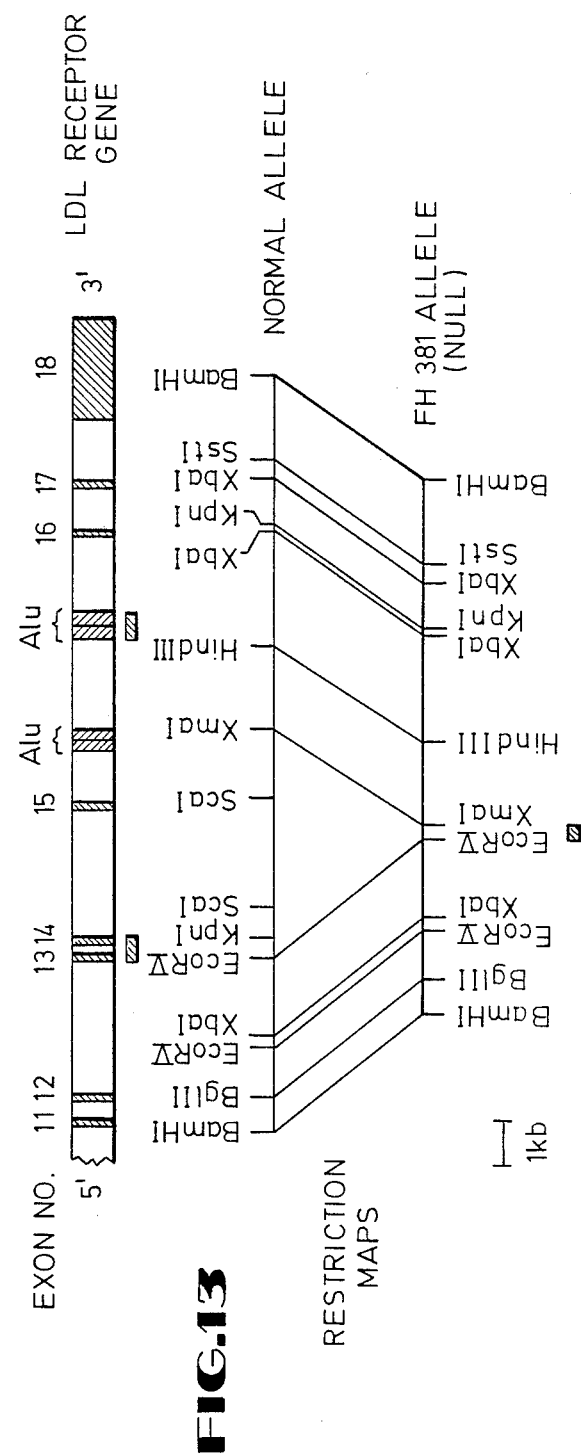
FIG. 13 is a comparison of restriction maps of the 3' end of the normal LDL receptor gene and the deletion-bearing gene from FH 381 DNA (mother of J.D.). Solid segments are exons and open segments are introns. Two clusters of Alu repetitive elements in intron 15 are indicated. Restriction enzyme recognition sites used to define the deletion in FH 381 DNA are shown. The map of the FH 381 allele was generated from lambda FH 381-10, which contains BamHI fragment C. Solid bars above or below the restriction maps denote segments of the normal and mutant genes that were used for DNA sequencing.

Genomic clones containing the null allele were restriction mapped and the results displayed in FIG. 13. FIG. 13 compares restriction maps of the normal 17-kb BamHI fragment and the 12-kb BamHI fragment that was cloned from FH 381 DNA. The FH 381 allele has an apparent deletion of 5 kb between an EcoRV site in exon 13 and an Xma I site in intron 15. As will be appreciated, deletion mutations of the sort exhibited by FH 381 can be successfully diagnosed by Southern blot hybridization using a wide variety of digesting enzymes. The preferred enzymes are those displayed in FIG. 13. However, any enzyme which releases a DNA fragment from the affected region, or which recognizes a site within the affected region, can be successfully used. Moreover, any DNA probe which contains a sequence capable of hybridizing to the affection gene regions may be employed. Most conveniently, this is pLDLR-2 which contains the LDL receptor cDNA.

EXAMPLE VIII

Mapping of FH 781-A Deletion Mutation Involving Exon 18

The present example is directed to an internalization-defective mutation that deletes the COOH-terminal end of the LDL receptor. This mutation occurred in a Japanese FH homozygote. Previous studies have shown that this individual produces LDL receptors that can be visualized on the cell surface, where they bind LDL but fail to migrate to coated pits. This individual appears to be a true FH homozygote, and not a genetic compound, since the parents were first cousins. Through use of genomic cloning and DNA sequencing techniques, the LDL receptor gene from this Japanese homozygote (designated FH 781 in the current study) was found to bear a deletion that joins intron 15 to exon 18. The Japanese mutation in FH 781 resembles the FH 274 mutation (see Example IV) in that it involves a recombination between two repetitive elements of the Alu family, one in intron 15 and the other in the non-coding region of exon 18. However, different Alu sequences and different mechanisms of recombination are believed to be involved in the two mutations.

Figure 14:
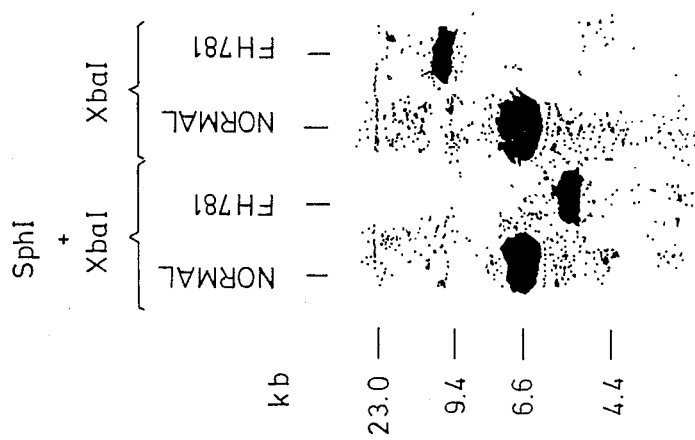
FIG. 14 is a southern blot hybridization of genomic DNA from normal and FH 781 individuals. Genomic DNA (5 ug) was isolated from cultured fibroblasts of the indicated subject and digested with XbaI alone or in combination with SphI. Fragments were subjected to electrophoresis, transferred to nitrocellulose, and hybridized with a $^{32}$P-labeled probe that corresponds to the 3' end of exon 18 (nucleotides 4965–5065 of the normal cDNA). Molecular size standards were generated by HindIII-cleavage of bacteriophage lambda DNA.

Blot hybridization of genomic DNA from subject FH 781 revealed an abnormal restriction fragment when the DNA was restricted with XbaI and probed with a $^{32}$P-labeled cDNA probe derived from the 3' end of exon 18 (FIG. 14). In DNA isolated from a normal subject, a 6.6-kb band is detected (Lane C), whereas the FH 781 DNA showed a 10.5-kb band (Lane D). Digestion with SphI did not reduce the size of the XbaI fragment in the normal DNA (Lane A), but it did reduce the size of the fragment produced by the FH 781 DNA (Lane B). One possible interpretation of this data is that the FH 781 DNA contains a deletion that removes an XbaI site, thereby joining two XbaI fragments. The resulting abnormally large XbaI fragment now includes an SphI site. Furthermore, the absence of fragments in the FH 781 digest that comigrate with the normal fragments suggests that this patient is a true FH homozygote.

Figure 15:
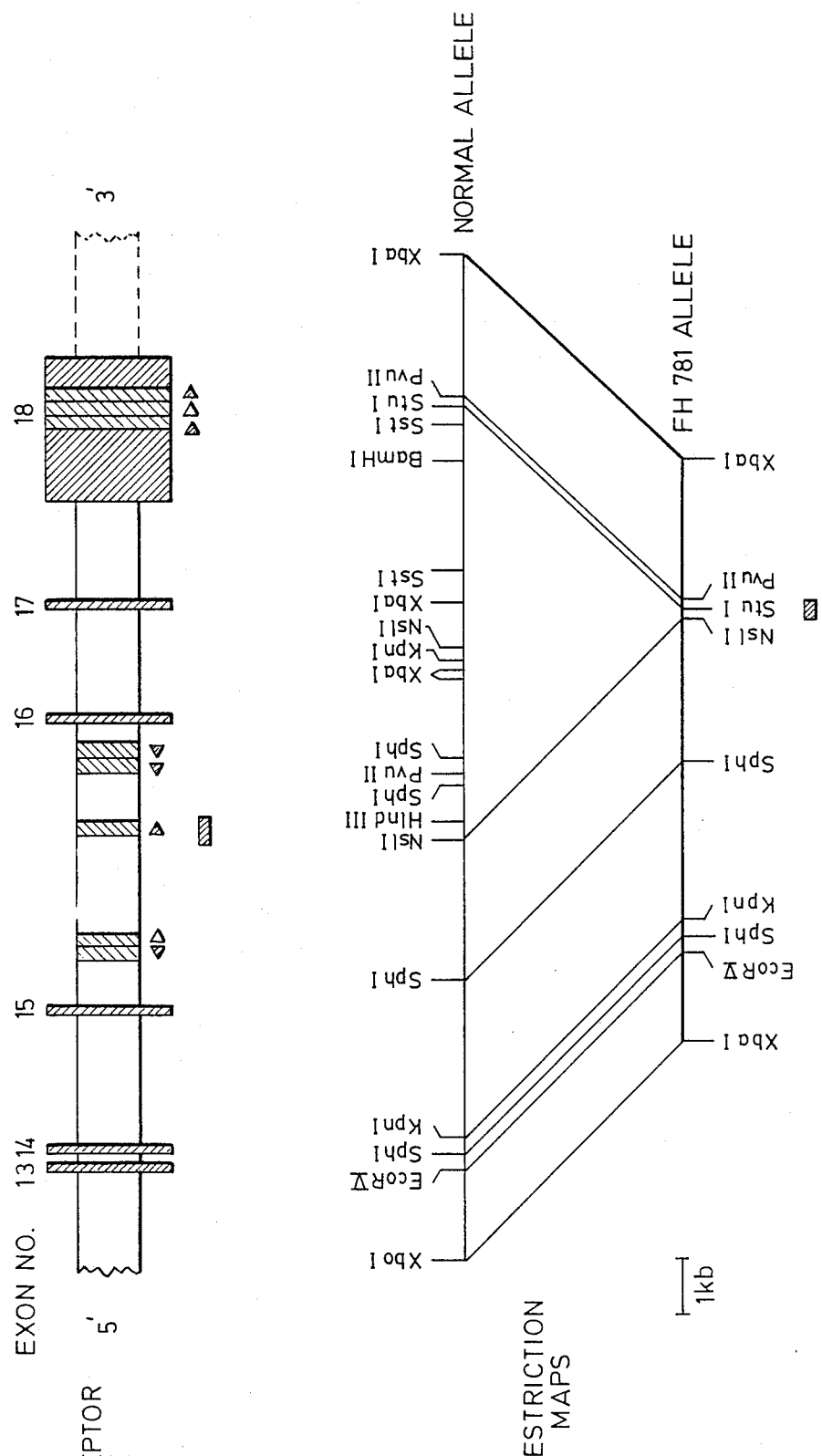
FIG. 15 is a comparison of restriction maps of the 3' end of the normal LDL receptor gene and the deletion-bearing gene from FH 781. Exons are indicated by solid vertical bars; introns are indicated by open segments; and known Alu repetitive elements in intron 15 and exon 18 are indicated by striped bars. Arrowheads indicate the relative orientation of each Alu sequence relative to the consensus structure and represent either complete (closed arrowhead) or half (open arrowhead) repeats. Restriction enzyme recognition sites used to define the deletion in FH 781 are shown; the StuI site shown was located by DNA sequencing. Solid bars above or below the restriction map denote segments that were subjected to DNA sequencing.

To learn more about this putative deletion, the abnormal XbaI fragment was isolated by cloning in bacteriophage lambda. FIG. 15 compares restriction maps of the cloned FH 781 insert and the 3' end of the normal LDL receptor gene as determined from a previously cloned fragment. The results indicate that the FH 781 allele harbors a deletion of approximately 7.8 kb that begins in the middle of intron 15 and terminates in the middle of exon 18. As with the preceding examples, the preferred enzymes for demonstrating this mutation is displayed in FIG. 15. However, as those of skill in the art will recognize, these are not the only enzymes which may be employed.

Figure 16A:
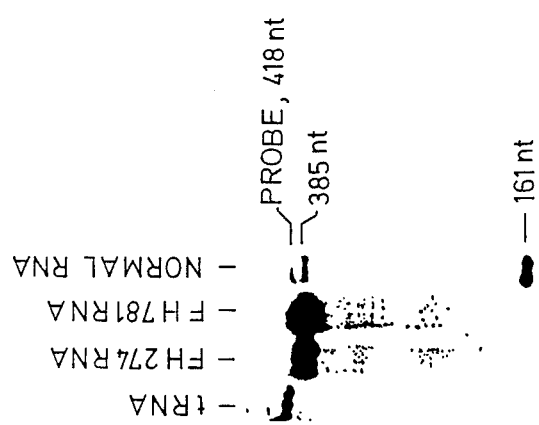
FIG. 16 illustrates the Sl nuclease mapping of exon 15 in normal and FH 274 and 781 mutant RNAs. A 0.38-kb PstI-NdeI fragment covering 161 base pairs of the 3' end of exon 15 plus 224 base pairs if the 5' end of intron 15 was subcloned into PstI and SmaI-digested M13mpll RF DNA, and a single stranded uniformly labeled $^{32}$P-labeled probe was prepared. The probe was hybridized with 25 ug of total cellular RNA from normal, FH 274, or FH 781 fibroblasts and then digested with Sl nuclease. The relative orientations of the protected fragments with respect to the probe are indicated at the bottom of the figure. nt, nucleotides. Molecular size standards were generated by HaeIII digestion of 0X174 replicative form DNA.
Figure 16B:
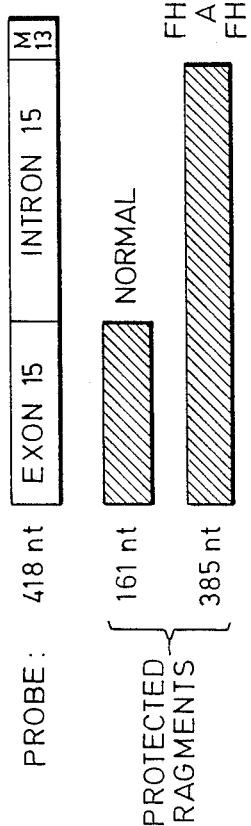

To test directly for the presence of intron 15 in the mRNA transcripts, an S1 nuclease analysis was performed (FIG. 16). Total RNA from normal, FH 274, and FH 781 cells was hybridized with a single-stranded uniformly labeled probe that contained 385 nucleotides that spanned the junction between exon 15 (161 nucleotides) and intron 15 (224 nucleotides). The probe also contained 33 nucleotides of M13 sequence. When RNA from normal cells was hybridized to this probe, S1 nuclease digestion gave rise to a protected fragment of 161 nucleotides, consistent with the removal of intron 15 by splicing. In the FH 274 and FH 781 RNA, there was no evidence for splicing at the exon 15/intron 15 junction. The protected fragment of 385 nucleotides indicated that the probe had hybridized to mRNA species in which exon 15 and intron 15 remained in continuity. (the small proportion of 385-nucleotide species observed in normal cells probably corresponds to unspliced nuclear RNA as total cellular RNA was used in these experiments). To test for the presence of other sequences in the mRNA downstream of exon 15, various probes (derived from the normal gene) were used in blot hybridization analysis of normal, FH 274, and FH 781 RNA. The two probes from exon 18 were found to hybridize with all three mRNAs. However, the two probes from intron 15 hybridized only with FH 274 and FH 781 transcripts, and not with the normal mRNA. These results are consistent with the predicted splicing pattern.

EXAMPLE IX

Diagnosis of FH 563 - A Small Deletion Involving Exon 4

The LDL receptor gene of FH 563, a homozygous FH subject, was found to contain a small deletion of about 7 to 12 amino acids in exon 4. Inasmuch as exon 4 encodes the fifth repeat in the cysteine-rich binding domain, the present data suggest that the transport-deficient receptor in FH 563 is produced by a mutation in this cysteine-rich region.

The particular mutation exhibited by FH 563 may be demonstrated either by the Southern blot approach or by the S1 nuclease approach. Again, any enzyme which releases a fragment spanning the exon 4 region, will demonstrate a difference in fragment length in the normal versus afflicted individual's DNA. However, due to the extremely small deletion, it was necessary to employ a gel system which was capable of distinguishing such a small difference, for example, a high percentage agarose gel (see example X below) or a polyacrylamide gel. The preferred enzyme for displaying this deletion is Taq I, in that this enzyme has only a 4 base-pair specificity and thus tends to release smaller fragments. In this manner, the existence of smaller deletions are more readily ascertained.

Alternatively, S1 nuclease mapping may be employed. The results of a typical experiment are shown in FIG. 17. FIG. 17 demonstrates the expression of normal and mutant LDL receptor mRNA's in human fibroblasts from FH 563 and his parents. LDL receptor mRNA's were detected by a solution hybridization-S1 nuclease assay. A uniformly $^{32}$P-labeled probe encompassing nucleotides 422 to 1007 of the human receptor mRNA (see FIG. 3) was prepared and annealed to the indicated RNA at 39° C. for 16 hrs. After digestion with 700 units of S1 nuclease for 1 hour at 37° C. and electrophoresis on denaturing polyacrylamide gels, nuclease-resistant hybrids were visualized by autoradiography.

Each hybridization reaction contained RNA isolated from the following cell strains induced for LDL receptor expression: (lane 1) no RNA; (Lane 2) 10 ug of total RNA from SV40-transformed normal human fibroblasts; (lane 3) 15 ug of total RNA from fibroblasts of the father of FH 563; (lane 4) 15 ug of total RNA from fibroblasts from the mother of FH 563; (lane 5) 10 ug of total RNA from fibroblasts of FH 563. The dried gel was exposed to Kodak XAR 5 film for 24 hours at −70° C. with a Dupont Cronex Lighting Plus screen. Size standards were generated by electrophoresis of a labeled Msp I digest of pBR322 DNA the results thus confirm the existence of the deletion.

In normal RNA, a protected fragment of 586 nt was detected (lane 2). However, in RNA isolated from FH 563 cells two smaller fragments of approximately 217 and 348 nt were detected together with a small amount of undigested heteroduplex (lane 5). RNA from the heterozygous parents of FH 563 showed roughly equal amounts of the normal protected fragment of 586 nt and the two abnormal protected fragments of 217 and 348 nt (lanes 3 and 4). These findings, together with those obtained with other probes, are consistent with the presence of a small deletion of about 7 to 12 amino acids in exon 4 of the LDL receptor gene.

EXAMPLE X

Diagnosis of the Lebanese Allele—A Nonsense Mutation

As noted above, the prevalence of homozygotes is generally about one in 1 million. However, in Lebanon the frequency of the homozygous condition is more than 10-fold higher. This is attributable to a high prevalence of heterozygosity for FH among Lebanese people, coupled with a high incidence of consanguinity which increases the proportion of homozygotes. It was through studies of the Lebanese population that Khachadurian first clearly delineated the existence of homozygous FH (Khachadurian (1964) *Am. J. Med.*, 37: 402). The molecular basis of the mutation in the LDL receptor gene that produces FH in the Lebanese population is unknown.

In the current example, the molecular basis of a prevalent mutation that causes FH in the Lebanese population is detailed. This "Lebanese allele" produces a receptor that migrates with an abnormally small apparent molecular weight of 100,000. The defect is attributable to a single base substitution in exon 14 that produces a premature termination codon. The truncated receptor lacks the region encoded by exon 15 and therefore lacks clustered 0-linked sugars. The receptor also lacks a membrane-spanning region and a cytoplasmic tail. Evidence for a similar defect was found in four individuals, three from different families in Lebanon and one from Syria. It is believed that this nonsense mutation accounts for the high frequency of FH in Lebanon.

The five subjects studied (FH 264, 550, 786, 793, and 787) have the classical clinical syndrome of dominantly inherited homozygous FH. FH 264 (female), FH 550 (female), and FH 786 (male) are from three different Lebanese families. FH 793 (female) is Syrian. Cells from all four of these subjects produce a 100-kDa LDL receptor precursor that is not processed.

FH 265 (male) is a Lebanese with a variant form of familial hypercholesterolemia. He is one of four affected siblings in the Kh family described by Khachadurian ((1971), *Protides Biol. Fluids*, 19: 315). The variant form of hypercholesterolemia is distinguished from classic FH in the following three ways: (1) autosomal recessive inheritance (the heterozygous parents in the Kh family have normal total plasma cholesterol levels); (2) lower total plasma cholesterol levels in affected homozygotes (the four affected siblings in the Kh family have values of 414–470 mg/dl versus 600 to 1000 mg/dl in classic FH homozygotes); and (3) a lower population frequency (of 30 families with severe hypercholesterolemia in Lebanon, only 1 had the variant form and the other 29 had classic FH).

Biochemical studies on fibroblasts cultures derived from the five subjects indicated the presence of LDL receptors having a reduced size, a lack of clustered 0-linked sugars, and an absence of reactivity with the anti-COOH-terminal antibody. This suggested that the FH 264 receptor might terminate prior to the region encoded by exon 15. To determine whether this termination resulted from a gross deletion in the FH 264 gene, the size of the mRNA encoded by this allele was studied. The size of the LDL receptor mRNA produced by the FH 264 cells was found to be indistinguishable from normal after agarose gel electrophoresis. Moreover, extensive analysis of the FH 264 receptor gene by Southern blotting with cDNA probes specific for exons 1-18 of the receptor indicated an absence of any large deletions or rearrangements. These findings suggested that the shortened receptor protein in the FH 264 cells was the product of a nonsense mutation occurring 5′ to exon 15 in the LDL receptor gene.

To test this hypothesis, genomic cloning of FH 264 DNA was initiated. In this manner, exons 11-17 (and part of exon 18) of the LDL receptor were found gto be contained on a 17-kb BamHI fragment. In particular, genomic DNA from patient FH 264 was digested with BamHI and fragments were size-fractionated to isolate those with a size in the range of 17 kb. DNAs were the ligated into a bacteriophage lambda cloning vector. A recombinant bacteriophage containing the receptor fragment was isolated, and the DNA insert was subcloned into pBR322 and subjected to sequencing by primer extension on denatured double-stranded DNA. The sequence of the extended primer was determined by the chemical method of Maxam and Gilbert and by the dideoxy chain termination method of Sanger, et al. Both methods gave the same result: the FH 264 gene contained a cytidine to adenine transversion in codon 660 of the mature receptor, changing the codon from TGC (cysteine) to TGA (termination).

The nucleotide substitution in FH 264 would be expected to create a new recognition site for the restriction enzyme HinfI. To confirm that this substitution was indeed present in genomic DNA and to determine whether the same mutation was present in other Lebanese FH homozygotes, a genomic blotting experiment was performed and is shown in FIG. 18A. Genomic DNA was digested with HinfI, subjected to electrophoresis on a 5% agarose gel, and blotted onto Zeta probe membranes, which efficiently retain small fragments of DNA. The blots were probed with a $^{32}$P-labeled cDNA fragment corresponding to exon 14. DNA from five normal subjects (two of whom are shown in FIG. 18A) showed a HinfI band of approximately 286 base pairs. In the three Lebanese patients and the one Syrian patient described above (FH 264, 550, 786, and 793), a smaller HinfI fragment of approximately 210 base pairs was seen (FIG. 18A). This is the predicted size of the fragment if the abnormal HinfI site were present in the gene (FIG. 18B). Moreover, the absence of the normal 286-base pair fragment indicates that all four individuals are true homozygotes. DNA from the Lebanese patient (FH 265) with the variant form of hypercholesterolemia showed only the normal HinfI band (FIG. 18A). This result is consistent with the biochemical phenotype of these cells, which shows a mature receptor that migrates with an apparent molecular weight of 160,000 on SDS gels.

Accordingly, the present example indicates that the HinfI enzyme, and any other enzyme capable of recognizing and cleaving at the site of the point mutation, is useful in the diagnosis of non-variant FH which results from the Lebanese allele mutation.

OVERVIEW

The preceding examples demonstrate the successful cloning and characterization of both the cDNA for the human LDL receptor protein (pLDLR-2) and various portions of the normal gene (for example, as illustrated by clones lambda 33-1, lambda 33-2, lambda Hl, lambda 21, cos 1, cos 26, lambda 25, lambda 34 and lambda 31). Various of these clones have been deposited with the ATCC as follows:

| ATCC NO. | DEPOSIT DATE | DESCRIPTION |
| --- | --- | --- |
| 39965 | 12/20/84 | *E. coli* bearing plasmid pLDLR-1 |
| 39966 | 12/20/84 | *E. coli* bearing plasmid pLDLR-2 |
| 40147 | 12/28/84 | Bacteriophage *lamda* 33-1 |
| 40148 | 12/28/84 | Bacteriophage *lamda* 33-2 |
| 40149 | 12/28/84 | Bacteriophage *lamda* hl |

Figure 19:
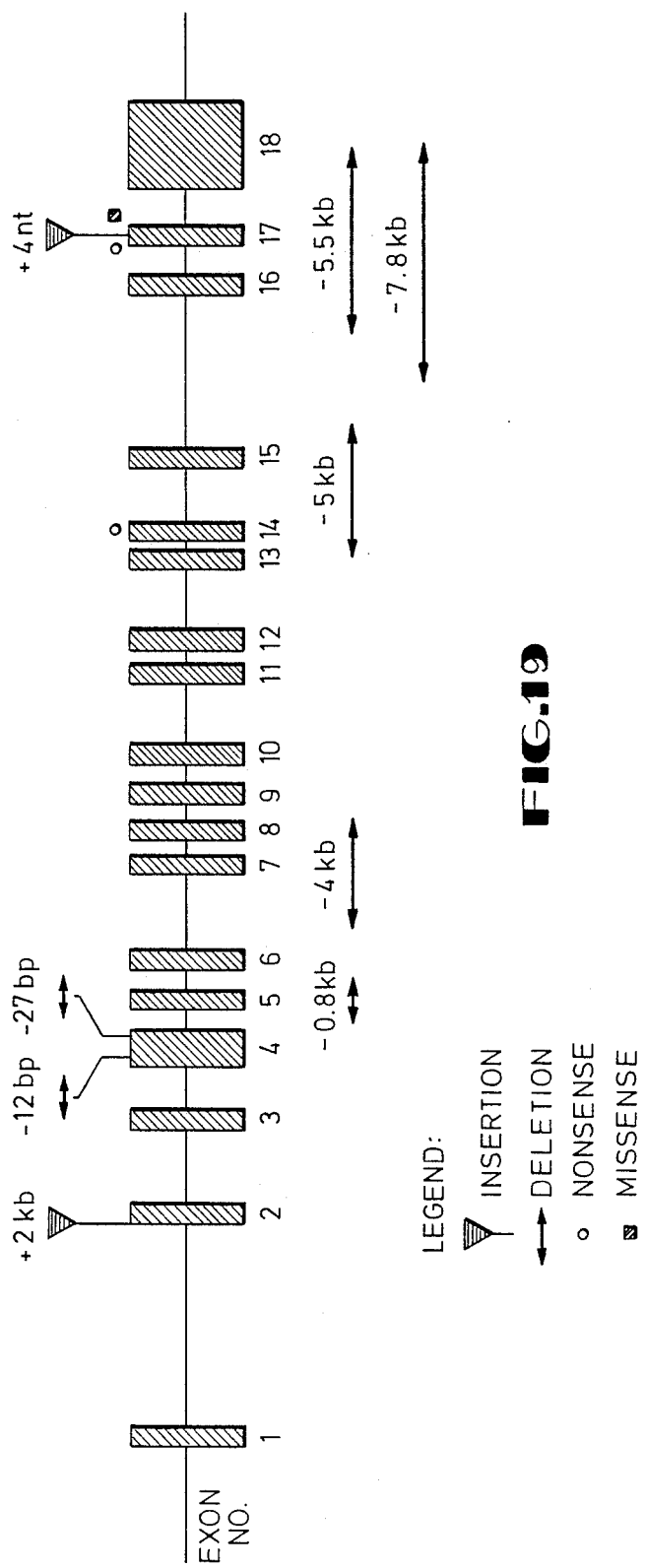
FIG. 19 is an overview of mutations in the LDL receptor gene. Exons are shown as hatched boxes and introns as the lines connecting them. The map is not drawn to scale. Mutations that have been mapped or cloned are indicated above and below the gene. The mutations are: 2kb insertion in intron 1 (FH 295), 12-base pair (bp) deletion in exon 4 (WHHL rabbit), 27-bp deletion in exon 4 (FH 563), nonsense mutation in exon 14 (FH 264, 550, 786, 793), nonsense mutation in exon 17 (FH 683), 4-bp insertion in exon 17 (FH 763), missense mutation in exon 17 (FH 380), deletion of 0.8 kb (FH 626), deletion of 4 kb (FH 359 and FH 454), deletion of 5 kb (FH 381), deletion of 7.8 kb (FH 781, and deletion of 5.5 kb (FH 274).

Moreover, the examples demonstrate and characterize the existence of a wide variety of mutations which result in FH in individuals homozyous or heterozygous for the particular mutation (summarized in FIG. 19). Although the examples present detailed characterization of the various mutations at a DNA structural level, such detailed characterization is not necessary for the diagnostic methods of the present invention. In this regard, the examples provide a relatively simple diagnostic procedures for testing for the presence of a structural mutation in a particular patient's FH gene.

The most straight forward procedure involves the Southern blot technique. In general terms applicable to most any insertion and deletion mutations, the technique involves specifically fragmenting DNA from cells of an individual suspected of carrying the mutation.

After the DNA is fragmented, the fragments are separated into patterns according to their physiochemical properties. In general, this will involve a size fractionation of the DNA fragments, for example, by gel electrophoresis. Once the DNA fragments are separated into patterns, the particular pattern of the LDL receptor gene fragments are identified, typically through hybridization with a labeled DNA fragment which corresponds to the LDL receptor gene. Therefore, the specific pattern of LDL receptor gene fragments are identified as a particular "fingerprint" of that individual's LDL receptor gene. Depending on the particular type and/or size of the mutation, the particular genetic fingerprint will be altered in a manner specific for the mutation. In any case, the FH "fingerprint" will be distinguishable from the normal LDL gene fingerprint, and therefore the technique is diagnostic for the presence of a mutation.

Where the mutation involves a large insertion or deletion (e.g.—greater than 100 base pairs) the fragmented DNA will normally be separated through the use of techniques suited to a discernable separation of larger DNA fragments, for example, low percentage (0.5–1%) agarose gel electrophoresis. However, as those of skill in the art will recognize, where a smaller deletion or insertion is suspected, one will typically utilize a separation medium which is capable of discerning smaller DNA fragment sizes, for example, high percentage (5%) agrose or polyacrylamide gel electrophoresis. Where the implicated mutation is, for example, a point mutation, one can sometimes identify an altered restriction enzyme recognition site, as in the case of the Lebanese allele. In such a case, the particular separation medium employed will depend on the size fragment released by the particular enzyme. Alternatively, point mutations in FH individuals can be diagnosed by oligonucleotide hybridization or by S1 nucleese analysis, as discussed in Examples I, II, VI, VIII and IX above.

Identification of an altered pattern in any of these techniques, as noted previously, is achieved by any labeled (for example radiolabeled or enzymatically tagged) DNA fragment which can hybridize to the LDL receptor gene, or more particularly, the fragments which are altered by the mutation. In general, all mutations can be identified using probes prepared from pLDLR-2, or fragments derived from the lamda and cos genomic clones (FIG. 7). The sequence of pLDLR-2 is illustrated in FIG. 3. Those of skill in the art will recognize that this sequence provides sufficient information for preparing particular DNA probes, which span particular regions of the gene. However, use of the entire pLDLR-2 is typically sufficient for Southern blot application.

The preceding examples additionally illustrate a further diagnostic technique useful in identifying FH mutations. This technique, termed single-strand nuclease mapping, requires the hybridization of total RNA from the test individual with a labeled DNA probe, followed by subjecting the resultant duplex to digestion with a single-strand specific nuclease. Where a proper duplex is formed (i.e.—homology between the test individual's DNA and the selected probe), no degradation of the probe occurs, therefore leaving the probe intact. However, where a mismatch occurs, as in the case of a deletion mutation, a noncontinuous duplex is formed, which results in a cleavage of the probe upon single-strand nuclease digestion. Therefore, all that is required for single-strand nuclease mapping of deletion mutations, is a probe which spans the affected region of the gene. For example, where a mutation involving exon 4 is suspected, the patients RNA is hybridized with a probe which spans the exon 4 region. Following hybridization, the duplex is subjected to single-strand specific nuclease. If the nuclease degrades the probe, than a mutation has been identified. Again, the sequence information provided by FIG. 3 will allow for the preparation of particular probes which may be used in such nuclease mapping.

The following table, Table III, lists the preferred enzymes which may be used in conjunction with the Southern blot diagnosis technique in diagnosing mutations of the LDL receptor gene. In addition, Table III provides information as to the particular exon involved in several mutations, and further the size of the particular fragment released by the enzyme in both the normal and FH gene. As those of skill in the art will recognize, Table III is illustrative of a preferred embodiment only and is further illustrative of the presently contemplated best mode.

a ligand such as biotin. In general, any specifically bindable ligand that is capable of being independently detected can be used. These and all other changes should be considered within the scope of the appended claims.

Although many of the particular cases disclosed were mutations resulting from a deletion, further extensions of the present invention can also detect mutations resulting from other types of events, including single nucleotide changes, as shown herein. The latter can be detected directly on Southern gel blots when they lead to the loss or acquisition of a resriction enzyme cleavage site. Single nucleotide changes can also be detected by their reduced hybridization with short segments of the cDNA for chemically synthesized oligonucleotides corresponding to the sequence of the cDNA. Weakened hybridization can be detected by the "melting" or dissociation of the mutant and normal DNA sequences after they have been hybridized to each other. Such abnormal melting behavior can be detected as an increased sensitivity to heat, lower ionic strength, or chemicals such as urea and formamide that dissociate chains of hybridized DNA. Thus, the present invention will be useful for the diagnosis of all potential mutations in the LDL receptor gene.

TABLE III

| | | DIAGNOSTIC DNA FRAGMENTS | | | |
|---|---|---|---|---|---|
| SUBJECT | MUTATION | PREFERRED ENZYME | AFFECTED REGION | NORMAL GENE | FH GENE |
| FH 295 | Insertion | EcoRI | Exon 7 | 8 kb | 11 kb |
| | | Asp718 | Exon 7 | 20 kb | 14 kb |
| FH 563 | Deletion | TaqI | Exon 4 | 164 kb | 137 bp |
| FH 626 | Deletion | EcoRI | Exons 5–7 | 8.5 kb | 13 kb |
| FH 359 | Deletion | EcoRI | Exon 10 | 8.8 kb | 5.4 kb |
| FH 381 | Deletion | BamHI | Exon 17 | 17 kb | 12 kb |
| FH 781 | Deletion | XbaI | Exon 18 | 6.6 kb | 10.5 kb |
| FH 274 | Deletion | XbaI | Exon 18 | 6.6 kb | 13 kb |
| FH 264, 550, 786, 793 | Missense | HinfI | Exon 14 | 286 bp | 210 bp |

The present invention has been disclosed in terms of examples considered by the inventors to be the preferred methods for practicing the invention. However, they are in no way meant to be the only modes of practicing this invention. For example, although the restriction enzyme XbaI was useful in exhibiting the particular mutation carried by FH 274, it is contemplated that the use of other restriction protocols may be necessary to display the specific mutation in other FH individuals. Similarly, although the present inventors feel that the Southern blot technique represents the best mode for displaying the pattern of LDL receptor gene fragments, other techniques should also work and should be considered as included within the scope of the present invention. For example, it would be possible to separate the fragments by column chromatography and assaying for the presence of gene fragments as they elute from the column. Similarly, although the probes used in the practice of the present invention have been radiolabeled, it is not considered that radiolabeling is the only technique whereby the probes may be rendered detectable. For example, DNA hybridization probes may be labeled with heavy isotopes or, alternatively, by binding

What is claimed is:

1. A method for diagnosing a mutation in the LDL receptor gene of an individual comprising the steps of:
   (a) fragmenting DNA from cells of the individual;
   (b) separating the DNA fragments into patterns according to their physicochemical properties
   (c) identifying the pattern of DNA fragments which correspond to the LDL receptor gene; and
   (d) diagnosing the mutation by identifying an alteration in the pattern of LDL receptor gene fragments of the individual relative to a pattern of normal LDL receptor gene fragments which have been fragmented in the same fashion.

2. The method of claim 1 wherein fragmenting the DNA comprises digesting the DNA with a preselected restriction endonuclease and step (b) comprises subjecting the fragmented DNA to electrophoresis.

3. The method of claim 1 wherein fragmenting the DNA comprises digesting the DNA with at least one restriction enzyme selected from the group consisting of Eco RI; Asp 718; Taq I; Bam HI; Xba I; Hinf I; Bgl II; Cla I; Eco RV; Kpn I; Pvu II; Sph I; Sst I; Sst II; Stu I; Xho I; Nde I; and Nsi I, and step (b) comprises subjecting the fragmented DNA to electrophoresis.

4. The method of claim 3 wherein the selected enzyme is Eco RI.

5. The method of claim 3 wherein the selected enzyme is Asp 718.

6. The method of claim 3 wherein the selected enzyme is Taq I.

7. The method of claim 3 wherein the selected enzyme is Bam HI.

8. The method of claim 3 wherein the selected enzyme is Xba I.

9. The method of claim 3 wherein the selected enzyme is Hinf I.

10. The method of claim 3 wherein the selected enzyme is Bgl II.

11. The method of claim 3 wherein the selected enzyme is Cla I.

12. The method of claim 3 wherein the selected enzyme is Eco RV.

13. The method of claim 3 wherein the selected enzyme is Kpn I.

14. The method of claim 3 wherein the selected enzyme is Pvu II.

15. The method of claim 3 wherein the selected enzyme is Sph I.

16. The method of claim 3 wherein the selected enzyme is Sst I.

17. The method of claim 3 wherein the selected enzyme is Sst II.

18. The method of claim 3 wherein the selected enzyme is Stu I.

19. The method of claim 3 wherein the selected enzyme is Xho I.

20. The method of claim 3 wherein the selected enzyme is Nde I.

21. The method of claim 3 wherein the selected enzyme is Nsi I.

22. The method of claim 1 wherein identifying the pattern of DNA fragments comprises hybridizing a labeled LDL receptor gene DNA fragment to the pattern of DNA fragments separated in step (b); and identifying the pattern of hybridized fragments by means of the label.

23. The method of claim 22 wherein the labeled DNA fragment comprises at least a hybridizable portion of a first DNA sequence which is complementary to at least a hybridizable portion of a second DNA fragment which codes for human LDL receptor protein.

24. The method of claim 22 wherein the labeled DNA fragment comprises at least a hybridizable portion of a fragment which codes for human LDL receptor protein.

25. The method of claim 22 wherein the labeled DNA fragment comprises at least a hybridizable portion of the DNA sequence of FIGS. 3A, B, C or D.

26. The method of claim 22 wherein the labeled DNA fragment comprises at least a hybridizable portion of the cDNA insert of pLDLR-2.

* * * * *